US009249508B2

(12) United States Patent
Braiman

(10) Patent No.: US 9,249,508 B2
(45) Date of Patent: Feb. 2, 2016

(54) BROMINE-SENSITIZED SOLAR PHOTOLYSIS OF CARBON DIOXIDE

(76) Inventor: Mark S. Braiman, Cazenovia, NY (US)

( * ) Notice: Subject to any disclaimer, the term of this patent is extended or adjusted under 35 U.S.C. 154(b) by 420 days.

(21) Appl. No.: 13/609,512

(22) Filed: Sep. 11, 2012

(65) Prior Publication Data

US 2013/0026028 A1     Jan. 31, 2013

Related U.S. Application Data

(63) Continuation-in-part of application No. PCT/US2011/028316, filed on Mar. 14, 2011.

(60) Provisional application No. 61/534,360, filed on Sep. 13, 2011, provisional application No. 61/452,152, filed on Mar. 13, 2011, provisional application No. 61/313,740, filed on Mar. 14, 2010.

(51) Int. Cl.

| | | |
|---|---|---|
| *C23C 18/12* | (2006.01) | |
| *C01B 31/10* | (2006.01) | |
| *C23C 16/48* | (2006.01) | |
| *B01D 53/62* | (2006.01) | |
| *C07D 305/04* | (2006.01) | |
| *C23C 16/26* | (2006.01) | |
| *C23C 18/14* | (2006.01) | |

(52) U.S. Cl.
CPC ............ *C23C 18/1245* (2013.01); *B01D 53/62* (2013.01); *C01B 31/10* (2013.01); *C07D 305/04* (2013.01); *C23C 16/26* (2013.01); *C23C 16/48* (2013.01); *C23C 16/482* (2013.01); *C23C 18/1204* (2013.01); *C23C 18/1208* (2013.01); *C23C 18/14* (2013.01); *Y10T 428/2991* (2015.01); *Y10T 428/2993* (2015.01); *Y10T 442/2992* (2015.04)

(58) Field of Classification Search
CPC ............ C23C 18/1245; C23C 18/1204; C23C 18/1208; C23C 18/14; C23C 16/48; C23C 16/482; C01B 31/08; C01B 31/10; B01D 53/62
See application file for complete search history.

(56) References Cited

U.S. PATENT DOCUMENTS

| | | | |
|---|---|---|---|
| 3,977,952 A | | 8/1976 | Knoevenagel et al. |
| 4,424,393 A | * | 1/1984 | Guzik et al. .................... 560/21 |
| 5,045,288 A | | 9/1991 | Raupp et al. |
| 5,184,020 A | * | 2/1993 | Hearst et al. ............. 250/455.11 |
| 5,854,967 A | | 12/1998 | Hearst et al. |

(Continued)

FOREIGN PATENT DOCUMENTS

KR        100944539        3/2010

OTHER PUBLICATIONS

Tanko (Science 263, pp. 203-205(1994)).*

(Continued)

*Primary Examiner* — Joel Horning
(74) *Attorney, Agent, or Firm* — Daniel Feigelson; Fourth Dimension IP

(57) ABSTRACT

There is described a process for depositing carbon on a surface, comprising, while contacting a mixture of $CO_2$ and $Br_2$ with a polar substrate presenting apposed surfaces, exposing a sufficient area of said mixture in the region of said apposed surfaces to light of sufficient intensity and frequency to result in deposition of carbon on at least some of said apposed surfaces. Other embodiments are also described.

20 Claims, 12 Drawing Sheets
(6 of 12 Drawing Sheet(s) Filed in Color)

(56) References Cited

U.S. PATENT DOCUMENTS

2006/0198029 A1* 9/2006 Schuster .................. 359/649
2007/0223096 A1* 9/2007 O'Connor et al. ............ 359/584

OTHER PUBLICATIONS

Hyatt (J. Org. Chem. 1984, 49, 5097-5101).*
Pathak (Green Chem., 2005, 7, 667-670).*
Kuwabata et al., J. Chem. Soc. Chem. Comm., (1995) 829-830.
Liu et al. (2007), Photochem. Photobiol. Sci. 6, 695-700.
Woolerton, et al., J. Am. Chem. Soc., 132, 2132-2133 (2010).
Licht et al., J. Phys. Chem. Lett. 1, 2363-2368 (2010).
Roeb et al. 2010, Science, 329. 773-774.
Peterson et al., Appl. Phys. Lett. 27, 305-307 (1975).
Bushong, (1896-96) Transactions of the Annual Meetings of the Kansas Academy of Science 15, 81-82 (1895-1896).
Walling and Padwa, J. Org. Chem. 27, 2976-2978 (1962).
Roscher and Nguyen, J. Org. Chem. 50, 716-717 (1985).
Kogure et al., J. Mol. Struct. 299, 105-109 (1993).
Seppelt, 1997, Acc. Chem. Res. 30: 111-113.

* cited by examiner

A

B

BROMINE-SENSITIZED SOLAR PHOTOLYSIS OF CARBON DIOXIDE

This application claims the benefit of priority from U.S. provisional application Nos. 61/313,740, 61/452,152 and 61/534,360, filed Mar. 14, 2010, Mar. 13, 2011 and Sep. 13, 2011, respectively, and is a continuation-in-part of PCT/US2011/028316, filed Mar. 14, 2011, the contents of all of which are incorporated herein by reference.

BACKGROUND

The predominant utilization of solar energy to drive the chemical reduction of atmospheric carbon dioxide is through photosynthesis by plants. This process reduces the level of the greenhouse gas in the atmosphere, and also leads to the formation of useful carbon-based fuels.

Achieving both of these goals with an industrial process is generally recognized as having great utility. This is especially true if the material inputs for such a process are inexpensive, and do not include large amounts of water. Such a hypothetical industrial process for solar-powered photochemical reduction of $CO_2$ could open up large non-productive areas of the Earth's surface, e.g. deserts, to utilization of the large amounts of solar energy that fall upon them. Toward this goal, a great deal of effort has been applied in attempting to discover inexpensive methods for using the energy of sunlight to carry out chemical reduction of carbon dioxide, with the formation of elemental oxygen along with a carbonaceous material—either elemental carbon, or (using an additional material input such as hydrogen), some compound of carbon that stores a similar amount of energy as elemental carbon.

Carbon dioxide itself is capable of absorbing only a tiny fraction of the wavelengths of the solar spectrum that reach the Earth's surface, and essentially none of the visible or UV wavelengths that are most likely to be able to initiate photochemical reactions. Thus, a major thrust of the research in solar energy conversion has been to develop sensitizing chemicals that are capable of absorbing solar photons, thereby creating a high-energy photochemical product, which then can carry out chemical reactions with $CO_2$ leading, ultimately, to the formation of molecules containing chemically-reduced carbon.

Known methods for photochemical reduction of $CO_2$ have generally involved transition-metal compounds, with or without organic dye sensitizers. In a number of examples, titanium dioxide (titania) has been used as both a nanoparticle support and as a surface-active electron transfer agent, in order to photochemically reduce $CO_2$. In several examples of this approach, cobalt phthalocyanine (CoPc) was used as a photosensitizer (Kuwabata et al., *J. Chem. Soc. Chem. Comm.*, (1995) 829-830; Liu et al. (2007), *Photochem. Photobiol. Sci.* 6, 695-700). In the first example, $CO_2$ reduction to methanol was achieved by using a non-aqueous solvent, polypropylene carbonate ester. In the second example, it was hypothesized that even in aqueous media, electron transfer could proceed directly from the CoPc photosensitizer's excited state to a weakly liganded $CO_2$ molecule. In this case, most of the product was formic acid, which is not directly useful as a fuel but has greater value as a feedstock for chemical synthesis of larger molecules.

Both of the cited examples demonstrate the chief shortcoming of existing methods. In particular, the CoPc sensitizer is a complex molecule that requires considerable energy to produce; adsorbing it to titania nanoparticles requires additional processing; and the yields of reduced-carbon product so far remain low. These workers [Liu et al 2007] reported that even under optimal conditions, the total yield of reduced carbon was about 1 millimole (i.e. 12 mg carbon) per gram of catalyst. It is therefore unclear whether the low yield from such a photocatalyst will lead to a net storage of solar energy, or whether this conversion could ever be economical given the likely high cost of synthesizing the CoPc sensitizer. Cobalt itself is relatively common (crustal abundance of 25 ppm), with a bulk cost of the element about $44 per kg. However the CoPc sensitizer used in this particular process requires considerable additional synthesis steps, and currently has a bulk cost of over $5000 per kg.

In a more recent example utilizing a different type of sensitizer, both a ruthenium-bis-pyridyl compound and the enzyme carbon monoxide dehydrogenase were attached to titania nanoparticles in order to achieve photoreduction of carbon dioxide to carbon monoxide [Woolerton, et al., *J. Am. Chem. Soc.*, 132, 2132-2133 (2010)]. A measure of the efficiency of such conversion systems is the turnover number of the photosensitizing agent. In this case, it was possible to achieve a turnover number of 250 mmol of $CO_2$ per gram of $TiO_2$ per hour. However, in this case the chemical complexity of the nanoparticles has been increased even further than with the CbPc. Here, not only is a small-molecule sensitizer required (the ruthenium complex), but also an enzyme. As in the preceding examples, the high energetic and economic costs of producing the sensitized nanoparticles are significant disadvantages. Ruthenium's crustal abundance is approximately 1 ppb; current worldwide annual production is only 30 tons. The bulk cost is $6500 per kg. Furthermore, this bulk ruthenium requires costly additional chemical processing with a bis-pyridyl moiety before it can be made into a suitable photosensitizing compound, which makes its overall cost even higher on a per-mole basis.

More recently, a different kind of solar-powered process (the "STEP" method), involving less expensive materials, has been developed to carry out conversion of carbon dioxide to its component elements [Licht et al., *J. Phys. Chem. Lett.* 1, 2363-2368 (2010)]. However, this process does not involve transfer of electrons to $CO_2$ from small-molecules, or even nanoparticles, but rather from a macroscopic metal electrode. In this case, carbon dioxide is initially dissolved in a molten lithium carbonate/lithium hydroxide salt, and its conversion to graphite and molecular oxygen occurs in an electrochemical cell operating at an elevated temperature of over 500° C.; at temperatures above 700° C. the main product is not graphite but carbon monoxide. This cell is solar-powered only in the sense that both the heat needed to maintain the high temperature, and the electricity used to drive the cell, can be derived from sunlight. That is, there is no intrinsic requirement for light in this process, which is fundamentally electrochemical and thermochemical, rather than photochemical. The use of solar energy in this process has the same challenging economic considerations as in the use of solar energy for other heating and electrical uses. Using other sources of energy (e.g. wind energy) might make more sense, not only from the point of view of economics but also in terms of maximizing the net carbon storage.

Yet another proposed method of using solar energy to chemically split $CO_2$ involves the use of iron or cerium oxides in a redox cycle to initially reduce $CO_2$ to CO, and then release $O_2$ upon heating [Roeb et al. 2010, *Science,* 329. 773-774]. This process bears some similarity to the STEP method, in that the proposed use of solar energy is to drive a process that is not intrinsically photochemical. In this case, rather, the process is purely thermal, requiring temperatures of 800-2000° C. in order to release $O_2$ from the oxide of iron or cerium. Thus, while the chemical reagent costs (e.g. for iron oxide) are extremely low, the capital costs required for thermal reactors capable of carrying out this high-temperature reaction, in a widely-distributed fashion over a large area of the Earth's surface, are likely to be formidable.

BRIEF DESCRIPTION OF THE INVENTION

There is provided in accordance with an embodiment of the present invention a process for depositing carbon on a surface, comprising, while contacting a mixture of $CO_2$ and $Br_2$ with a polar substrate presenting apposed surfaces, exposing a sufficient area of said mixture in the region of said apposed surfaces to light of sufficient intensity and frequency to result in deposition of carbon on at least some of said apposed surfaces. In some embodiments, the polar substrate is a non-carbonaceous polar substrate. In some embodiments, the polar substrate is selected from the group consisting of silica, silica-based glasses, alumina and titania, and mixtures thereof. In some embodiments, the polar substrate is in particulate form. In some embodiments, the polar substrate is selected from sand, silica gel, powdered alumina, titania, quartz sand, glass spheres, and glass wool. In some embodiments, the light is a mixture of UV and visible light. In some embodiments, the mixture of UV and visible light includes light in the wavelength range of 300 to 500 nm. In some embodiments, the light is provided as sunlight. In some embodiments, the sunlight is focused onto said mixture in said region of said apposed surfaces. In some embodiments, the sunlight is focused using a parabolic or paraboloid mirror. In some embodiments the parabolic or paraboloid mirror is equipped to track the motion of the sun. In some embodiments, the polar substrate, $CO_2$ and $Br_2$ and are contained in a UV- and visible-light transparent region of a reaction vessel. In some embodiments, the range of transparency includes wavelengths of light from 300 to 500 nm. In some embodiments, the reaction vessel is made from quartz or borosilicate glass. In some embodiments, the pressure in the reaction vessel is between 1 and 71 bar. In some embodiments, the $CO_2$ is predominantly in the form of a gaseous phase. In some embodiments, the $CO_2$ is predominantly in the form of a liquid phase. In some embodiments, the ratio of $Br_2$ to $CO_2$ is between 1:1 and 1:1000 by weight.

There is also provided, in accordance with an embodiment of the invention, a composition of matter comprising a polar substrate presenting apposed surfaces and a mixture of $CO_2$ and $Br_2$ in contact with at least some of said apposed surfaces. In some embodiments, the polar substrate is a non-carbonaceous polar substrate. In some embodiments, the polar substrate is selected from the group consisting of silica, silica-based glasses, alumina and titania, and mixtures thereof. In some embodiments, the polar substrate is in particulate form. In some embodiments, the polar substrate is selected from sand, silica gel, powdered alumina, titania, quartz sand, glass spheres, and glass wool (fiberglass). In some embodiments, the polar substrate, $CO_2$ and $Br_2$ and are contained in a UV- and visible-light transparent region of a reaction vessel. In some embodiments, the UV- and visible-light transparent region is transparent to light having a wavelength of 300 to 500 nm. In some embodiments, the reaction vessel is made from quartz or borosilicate glass. In some embodiments, the pressure in the reaction vessel is between 1 and 71 bar. In some embodiments, the $CO_2$ is predominantly in the form of a gaseous phase. In some embodiments, the $CO_2$ is predominantly in the form of a liquid phase. In some embodiments, the ratio of $Br_2$ to $CO_2$ is between 1:1000 and 1:1 by weight.

There is also provided, in accordance with an embodiment of the invention, a composition of matter comprising a polar substrate presenting apposed surfaces and a material which is predominantly elemental carbon deposited on a portion of said apposed surfaces. In some embodiments, the molar ratio of bromine to carbon in said material is less than 1:12. In some embodiments the molar ratio of bromine to carbon in said material is from 0:12 to 1:12. In some embodiments, the composition of matter has been formed by a process in accordance with an embodiment of the invention.

There is also provided, in accordance with an embodiment of the invention, a process comprising isolating material which is predominantly elemental carbon from a composition of matter in accordance with an embodiment of the invention.

There is also provided, in accordance with an embodiment of the invention, a reactor for utilizing sunlight and bromine to reduce $CO_2$, the reactor comprising a reaction vessel and a sunlight focuser, at least a region of the reaction vessel being transparent to UV and visible light and said focuser focusing at least some of said sunlight on said region. In some embodiments said region of the reaction vessel is transparent to light in at least the range of 300-500 nm wavelength. In some embodiments, the reaction vessel is capable of withstanding an internal pressure of at least from 0 to 71 bar. In some embodiments, the reaction vessel is constructed at least in part from quartz or borosilicate glass. In some embodiments, the reactor further comprises a cooling mechanism for cooling a portion of the reaction vessel. In some embodiments, the reaction vessel is configured to hold a mixture of $Br_2$ and $CO_2$ in contact with a polar substrate having apposed surfaces in said region. In some embodiments, the reaction vessel contains a mixture of $Br_2$ and $CO_2$ in contact with a polar substrate having apposed surfaces. In some embodiments, the focuser is a parabolic or paraboloid mirror. In some embodiments the reactor is equipped to track the motion of the sun so as to keep the sunlight focused on said region of the reaction vessel as the Earth rotates.

There is also provided, in accordance with an embodiment of the invention, a composition of matter comprising a chemical compound of the formula $C_2O_44Br_4$. In some embodiments, the chemical compound of formula $C_2O_44Br_4$ is a substituted 1,3-dioxetane. In some embodiments, the substituted 1,3-dioxetane is 2,4-dibromo-2,4-dihypobromo-1,3-dioxetane. In some embodiments, the 2,4-dibromo-2,4-dihypobromo-1,3-dioxetane has the two hypobromo groups in a trans configuration; in other embodiments the two hypobromo groups are in a cis configuration. In some embodiment, the composition of matter consists essentially of the compound of the formula $C_2O_44Br_4$.

DETAILED DESCRIPTION

The invention described herein solves some of the problems with existing solar-powered reactions for chemical reduction of carbon dioxide. In particular, the claimed process works well at temperatures near room temperature. The process also utilizes an inexpensive material as a photosensitizer, viz. liquid $Br_2$. To the best of the inventor's knowledge, this material has never previously been identified as being chemically reactive with $CO_2$, but it has been sold for nearly 100 years as a commodity on worldwide markets. Its current production level, about a half-million metric tons annually, is more than 10,000 times that of ruthenium. Its 2009 bulk price was only a bit over $1000 per metric ton (corresponding to $1 per kg, or about 1/6000 the cost of elemental ruthenium, or of CoPc photosensitizer). The overall content of bromine in the Earth's crust is 0.3 ppm, or 100 times that of ruthenium. Elemental bromine can easily be produced in most countries on Earth from sea water, which is 70 ppm bromine. However, its richest source on Earth is the contents of the Dead Sea, which is 5% bromine by weight. Indeed, Israel and the US each produce about 40% of the worlds elemental bromine, with China accounting for most of the rest. Furthermore, unlike complex photosensitizers based on transition metals such as ruthenium or cobalt, elemental bromine itself strongly absorbs visible light, and therefore it can work directly as a photosensitizer for solar-powered photoreduction of $CO_2$, as described herein. Other than $Br_2$ and $CO_2$, the process requires only a polar substrate presenting apposed surfaces, such as particulate or fibrous silica, titania or alumina; a reaction vessel capable of holding these materials at an elevated pressure; and light of sufficient energy and intensity, such as can be obtained in focused sunlight. It will also be appreciated that in this description, when reference is made to a reaction vessel or the like that is transparent to UV and/or visible light, such transparency will generally be across the entire UV and visible range, but need not necessarily be so, provided that the transparency is through a range of wavelengths sufficient to enable the reaction to proceed.

The patent or application file contains at least one drawing executed in color. Copies of this patent or patent application publication with color drawing(s) will be provided by the Office upon request and payment of the necessary fee. Embodiments of the invention will be better understood with reference to the figures, in which.

Figure 1:
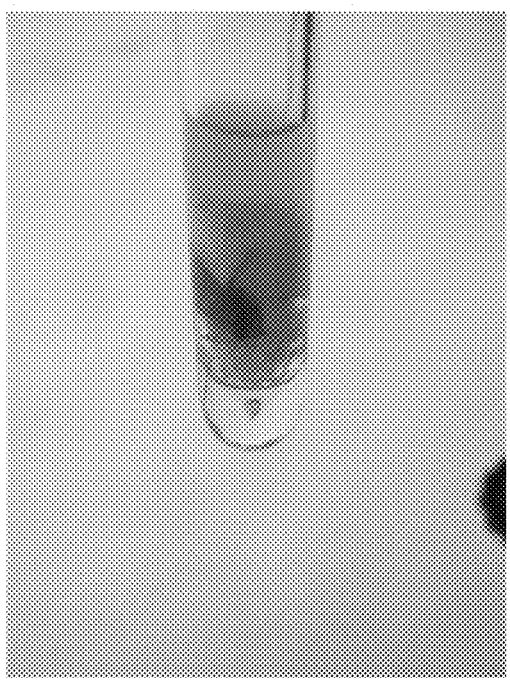
FIGS. 1A and 1B are photographs of a reaction vessel after reaction of molecular bromine and $CO_2$ in accordance with an embodiment of the invention.
Figure 1:
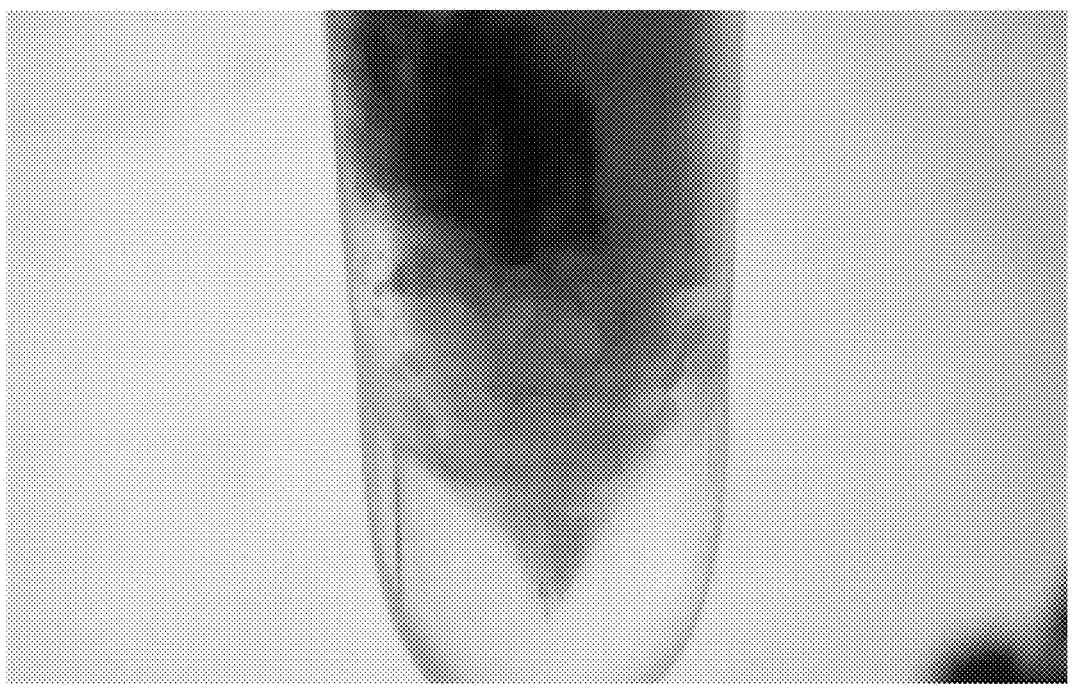

It will be appreciated that despite the prevalence of color drawings and photographs in the scientific literature and the ease of presentation of such in electronic format, PCT rules remain mired in the 19th century and still do not permit the filing of color drawings or photographs. Therefore FIGS. 1A, 1B, 3, 4 and 5 were filed in the parent PCT application (PCT/US2011/028316) as grayscale photographs. However, the original photographs are in color and, for the purpose of making them publicly available, were uploaded to a publicly-available picture sharing service, Shutterfly; the details of how to access that picture sharing service are recited in the parent PCT application. The color photographs were incorporated into the PCT application by reference, and, noted above, were filed as part of the present application.

Without wishing to be bound by theory, it is surmised that the presently claimed invention, in various embodiments thereof, facilitates the utilization of solar energy to split $CO_2$ into a solid species containing chemically-reduced carbon, and $O_2$. Although the elemental analysis results obtained to date provide a direct demonstration only of the deposition of a solid material containing carbon, as a black film, on surfaces of crystalline alumina, titania, silica, or silica-based glasses, the concomitant formation of elemental oxygen is an inescapable conclusion based on well-established chemical principles (see below, under Identity of the Oxidized Photoproduct).

General Methods.

In all cases discussed herein, a sample of $CO_2$ was contained within a UV- and visible-light-transparent photoreaction vessel that, along with its closure, was capable of withstanding substantial elevated internal pressure. In use, the reaction vessel also contained an amount of liquid $Br_2$ sufficient to provide a final ratio of between 1:1 and 1000:1 (weight ratio of $CO_2:Br_2$). Additionally, the reaction vessel contained a finely divided polar solid material, which provided spaces where apposed surfaces of these materials occur with spacing of only a few molecules apart (i.e. under ~100 nm). As discussed below, such closely-spaced polar surfaces appear to facilitate the deposition of stable carbonaceous solids from the photolysis reaction.

No commercially available closures or quartz tubing of adequate diameter (~10 mm) are rated to high pressures approaching the critical pressure of $CO_2$ (71 bar). Testing a number of hand-blown transparent glass containers for such a capability was determined by carefully warming small samples of $CO_2$ in each closed container, starting at dry ice temperature, and going up to and just beyond the critical temperature (~31° C.) while the container was kept safely behind a clear plastic shield. When container/closure combinations were found with suitable pressure-containment capabilities, the closures were then also checked for chemical compatibility with solutions of $Br_2$ in $CO_2$, by adding ~10 nl of liquid $Br_2$ to the bottom of the container, prior to addition of dry ice, sealing, and warming to ~31° C., for several h, again behind a clear plastic shield. Only custom-made vials, based on GL-14-threaded fused-silica tubing from Technical Glass Products, or GL-14-threaded borosilicate tubing from ChemGlass, all with internal diameters under 1 cm, were found to be suitable for these experiments.

Prior to transfers of $Br_2$ and $CO_2$, the reaction vessels were thoroughly cleaned, and dried at room temperature. In each instance, a sample of silica gel (Sorbent silica gel, 40-70 micron particle size), powdered alumina (Woelm), titania, quartz sand, glass spheres, and/or glass wool was added to the bottom 1-3 mL of the container (quartz or borosilicate tube). Subsequently each reaction tube and its contents of polar solids were generally dried further at 80° C. for 2-48 h under a stream of dry air. However, this more rigorous removal of water was omitted on several occasions, without any evident adverse results.

The $CO_2$ sample is most easily obtained, stored, and handled as a solid, i.e. as a block or chunk of dry ice, which is commercially available in this form to the general public from numerous sources. A chunk of dry ice is broken up into particles small enough to fit through the ~5-mm-diameter neck of the reaction vessel, immediately prior to transfer so as to minimize formation of water (frost) on its surfaces; crushing the $CO_2$ in a polyethylene bag also helps limit the formation of frost on the surfaces of the crushed $CO_2$. Although solid $CO_2$ is the most convenient form to use for implementation on a small (<5 g) scale, in principle the $CO_2$ may be supplied as a gas. $Br_2$ is easily generated as needed in small quantities by mixing similar masses of solid NaBr and $MnO_2$ in a glass vessel, adding concentrated sulfuric acid, and then distilling, with collection of the red $Br_2$ distillate into a dry-ice-chilled vessel. As with solid $CO_2$, these are readily available materials, even to the general public. In fact, for experiment #1 below, the NaBr was obtained in a standard commercial packet sold at a swimming pool supply company; the concentrated sulfuric acid was a commercial drain cleaner; and the $MnO_2$ was obtained from a sliced-open, unused standard AA-size 1.5V alkaline battery. A measured volume of $Br_2$ may be added on top of the dry ice, using a glass micropipette.

On a ~5-g scale, a preferred embodiment of a small-scale photoreaction vessel is a ~1-cm outer diameter, ~10-cm-long fused-silica (quartz) test tube with a standard GL14 thread (ISO designation of a standard glass thread), combined with a GL14 cap closure with a poly-tetrafluoroethylene (PTFE) seal. In experiments 1-3 described below, the actual vessel (see FIGS. 1A and 1B) was manufactured from commercially-available quartz tubing with a GL14 thread at one end, with the other end being sealed by a professional glass blower. Rough calculations (not shown) had suggested that it would be necessary to include light in the ultraviolet range in order to achieve bromine-sensitized photolysis of carbon dioxide. Subsequent experimentation (described below) seems to support this hypothesis. Therefore, it is believed that containers that are transparent to visible light, but not UV light, are unsuitable. Subsequent tests on threaded borosilicate tubes have shown that for wall thicknesses of up to at least ~4 mm, it was possible to transmit sufficient UV light through the borosilicate glass, in order to achieve bromine-sensitized photolysis of carbon dioxide (see experiments 4-6 below, and FIG. 5).

Attempts to use quartz reaction vessels that had been thermally fused to less-expensive threaded borosilicate glass tubing were a failure. Such hybrid vessels shattered when exposed to high pressures of liquid $CO_2$ near ambient temperature, most likely due to mismatch of thermal expansion coefficients at the joint between unlike glasses.

Likewise, not all GL14 cap closures were found to be suitable for containing the high-pressure liquid $CO_2$. The most consistently successful results were with GL14 caps from ChemGlass®. Caps from at least one other supplier, having a similar outward appearance, failed rather spectacularly at pressures near room temperature, by blowing out a disc of red plastic covering nearly the full diameter of the cap. This failure may be due to a different composition of the cap liners, which in the latter case are not composed entirely of PTFE, but rather consist of a thin film of PTFE fused to a ~1-mm thick silicone disc.

It was also found that commercially-available conical-bottom microreaction vessels (specifically 1-mL Reacti-Vials® from Pierce) were strong enough to hold liquid $CO_2$ samples. However, no closures available for these containers were found to be capable of sealing them for more than a few minutes at a time, when they contained a liquid $CO_2$ phase. Their thicker walls resulted in poorer focusing of sunlight onto the samples contained within them, and thus such samples never produced more than small amounts of stable dark carbonaceous product from the solar photolysis reaction. Nevertheless, Reacti-Vials, along with solid plastic caps and PTFE-laminated silicone liners, were found to be suitable for carrying out small-volume photoreactions for producing small quantities of the transient red photoproduct (described below), e.g. for mass spectrometry studies.

For larger-scale implementation, it is expected that $CO_2$ will be most easily transported as a liquid, gas, or supercritical fluid, either in pipes or in pressurized vessels at ambient temperatures, and that it will remain in one of these fluid forms during its transfer into a larger photoreaction vessel. Likewise, it is expected that larger reaction vessels will be mostly metallic, e.g. stainless steel, with high-pressure couplings to permit feeding of fluid $CO_2$ and $Br_2$, and containing tightly-sealed UV-transparent windows through which sunlight can be suitably focused.

For successful photochemical production of carbon from $CO_2$, as evidenced by formation of a black film at the point of illumination, it has generally been found to be beneficial to use a device for concentrating sunlight to at least several hundred times its natural intensity at the Earth's surface. The device used initially (see experiments 1-3) was a 45-degree off-axis paraboloid mirror, specifically a first-surface aluminized mirror with a ~25 mm focal length and numerical aperture of ~0.6. This was a detector-condenser mirror that had been removed, along with its mount, from a discarded Nicolet 60SX infrared spectrometer. Although theoretically capable of producing a focused solar spot size of 0.2 mm, observed spot sizes with this mirror were more typically ~1 mm.

Figure 7:
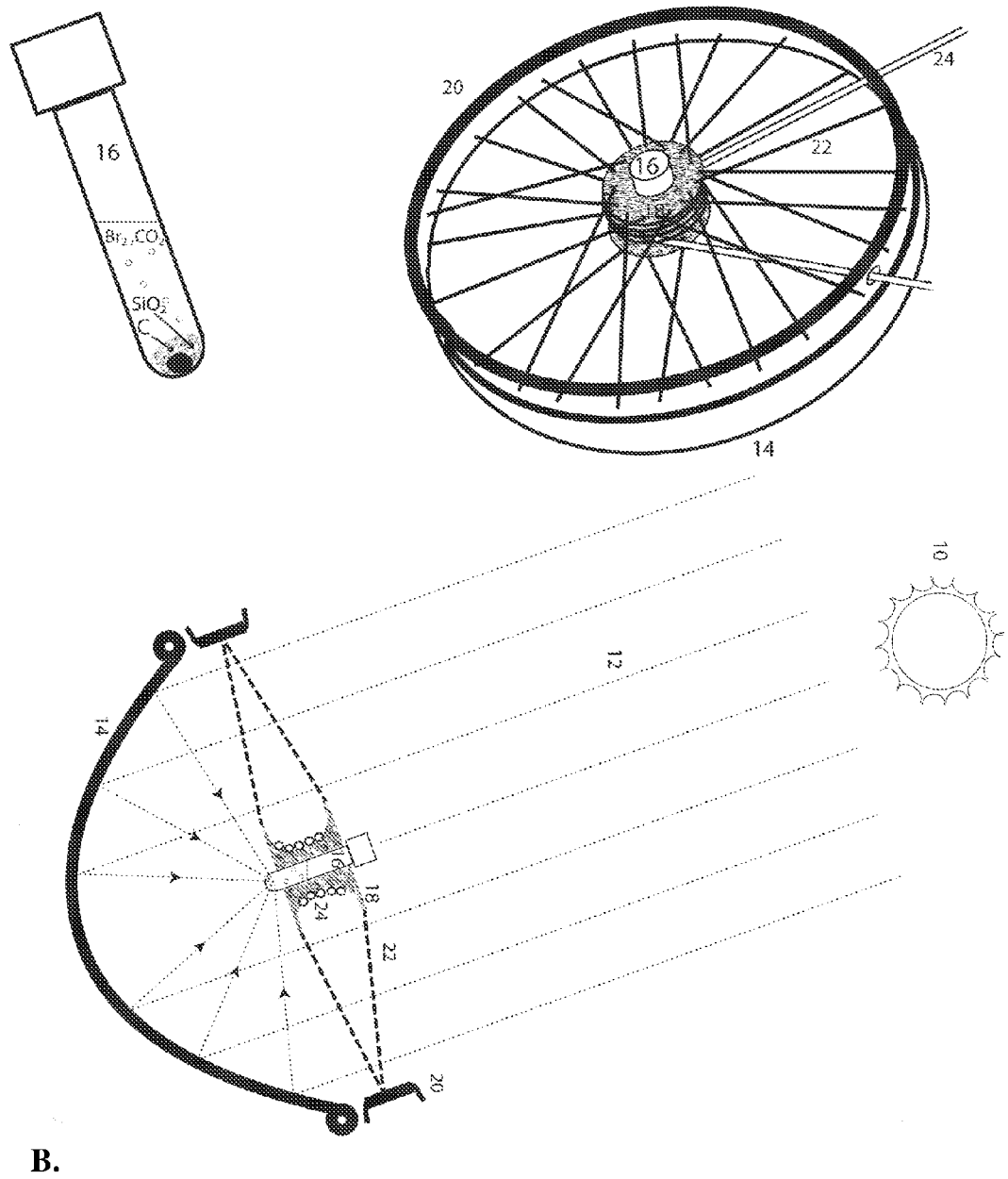
FIGS. 7A and 7B are perspective and cross-sectional views of a reactor constructed and operative in accordance with embodiments of the invention.
FIG. 7C is a cross-sectional view of a reaction vessel constructed and operative in accordance with embodiments of the invention and containing silicon dioxide, $Br_2$ and $CO_2$.

Subsequently, for scale-up, larger reflective optics were used successfully, including 12-inch and 24-inch diameter paraboloid reflectors (purchased from Edmund Optics, model nos. CS53-875 and CS53-876; see Experiments 4-6 below, and FIG. 4), and a 6-inch diameter molded plastic paraboloid reflector obtained from a car/truck headlamp (not shown). This is shown schematically in FIGS. 7A, 7B and 7C. FIG. 7A corresponds to FIG. 4, but is presented as a line drawing; FIG. 7B is a cross-sectional view of the same apparatus. Removable reaction vessel 16, which is shown in a larger view in FIG. 7C and containing $Br_2$, $CO_2$ and silicon dioxide, is held in place by the hub 18 of bicycle wheel 20; hub 18 is itself held in place by a plurality of spokes 22. The bottom of reaction vessel 16 protrudes through the bottom of the hub so that sunlight 12 can be focused thereupon by paraboloid reflector 14. The upper part of reaction vessel 16 remains inside hub 18. Inserted through the rim of the wheel is copper tubing 24, which wraps several times around hub 18 and then exits the wheel. Tubing 24, which is soldered to hub 18 using silver to maximize thermal contact therewith, may carry circulating coolant (e.g. ice water) therethrough, thereby cooling the upper part reaction vessel 16. Thus, when the liquid mixture of $Br_2$ and $CO_2$ in the reaction vessel boils as a result of heating from exposure to the focused solar radiation, the cooled upper part of the reaction vessel acts as a reflux chamber, resulting in condensation of the mixture. The two larger paraboloid reflectors nominally had somewhat larger numerical apertures than the small 45-degree reflector, but were not highly polished, and therefore typically produced spot sizes of 4-5 mm in diameter, i.e. considerably larger than indicated by their focal lengths (which corresponded to theoretical focused solar spot sizes of 0.6 and 1.2 mm, respectively).

For the sake of completeness, it will be mentioned that attempts to use a 25-mm diameter quartz asphere condenser lens with UV antireflection coating (obtained from Edmund Optics) as a solar concentrator have so far been unsuccessful. This may have been due to the >5-fold smaller surface area of this particular lens for collection of solar energy, as compared to the off-axis paraboloid mirror, and thus too large a reduction in the total energy available at the focal point. Without wishing to be bound by theory, it appears that in order to practice the claimed process, not only the solar intensity, but the total energy at the focal point must reach a certain threshold in order to initiate the photolysis reaction.

In some embodiments, it is useful to maintain a fixed focal point for the intense sunlight relative to the sample, even as the sun travels across the sky. For example, during illumination of the sample using sunlight coming from an elevation of less than 30 degrees above the horizon, initiation of carbon deposition at the focal point required in excess of 10 s of continuous illumination, even with a tightly focused solar image size approaching the ~0.2 mm value predicted for an imaging optic having a focal length of ~25 mm. The apparent motion of the sun across the sky is as high as ~15 degrees per hour, or approximately 0.5 degrees (the angular extent of the sun) every 2 minutes. (Of course, this maximum angular motion of the sun typically only occurs near the equator, except on the vernal and autumnal equinoxes, when it is observed everywhere on Earth, including the poles. On other days or locations, the apparent angular motion can be considerably less.). With a stationary focusing optic, the focused image of the sun is therefore expected to be quickly displaced by a distance equal to its diameter, i.e. in as little as 2 minutes. Thus the ability to rotate the sample and focusing optic together, along an axis parallel to the Earth's rotation axis, is helpful for maintaining good focused solar intensity, and in some embodiments of the invention the reaction apparatus is adapted track the movement of the sun so as to facilitate continuous focusing on the reaction vessel.

In experiments 1-4 described below, the device used to for rotating the sample and focusing optic simultaneously, thereby maintaining a fixed location of the focused solar image upon the sample, was a hobbyists' telescope equatorial mount and tripod, obtained from Tasco. The telescope itself was removed from the equatorial mount by removing its mounting screws. Then a custom-made aluminum mounting plate, with threaded holes for attaching both the focusing optic mount and the sample holder, was mechanically affixed to the equatorial mount. The equatorial mount's elevation angle clamp was adjusted to correspond to the latitude of usage (43 degrees N). The correct elevation angle was reproducibly obtained to within about 1 degree, simply by leveling the tripod mount with reference to the built-in bubble level. Meanwhile, by referring to a surveyor's map, the direction of true north was determined, relative to an exterior wall of a nearby building which was within ~5 degrees of north-south. This exterior wall was then used during all subsequent experiments as an azimuthal reference for positioning the tripod of the equatorial mount. The bubble-level and azimuthal references permitted the rapid and consistent visual alignment of the equatorial mount's rotation axis, to within ~2 degrees of parallel to the Earth's rotation axis. This in turn permitted tracking of the sun across the sky for periods of up to 20-30 min by adjustment of a single manual screw-knob on the equatorial mount; and for periods up to several hours with additional minor adjustments to a second screw-knob adjustment on the equatorial mount.

In Experiments 5-6 described below, the paraboloid reflectors were too large to be mounted on the same equatorial telescope mount used in experiments 1-3. However, their larger size and cylindrical symmetry facilitated pointing them accurately toward the sun while being hand-held. These reflectors all had circular holes at their rear, centered on the paraboloid axis. Furthermore, these reflectors were equipped with symmetrical sample-mounts that held the reactor vial along the same axis (see FIG. 4 for an example of the mounting device used, which was based on a simple bicycle wheel clamped to the outside of the paraboloid reflector). Thus, these reflectors could easily be aligned to point their axis directly towards the sun, simply by insuring that the shadow of the sample holder was centered on the rear hole in the reflector.

More precise alignment was achieved by maximizing the solar intensity focused onto the bottom of the reaction tube, the portion of the reaction tube in which the polar substrate was located and arranged closest to the reflector. This was monitored by using a small hand-held inspection mirror, inserted between the bottom of the reaction vial and the hole in the back end of the paraboloid reflector.

Scanning electron micrographs were obtained at the SUNY-ESF electron microscope facility. Samples were placed directly on the grids, and were sufficiently conductive that no shadowing was necessary. All mass spectrometry measurements were performed on a Thermo Polaris Q GC-MS instrument. Small amounts of each sample were transferred on fragments of glass wool, from the photoreaction vessel, into the pre-cooled solids probe of a GC-MS instrument, then allowing this sample to vaporize and ionize while bypassing the gas chromatograph. Unless otherwise noted, measurements were performed with an initial temperature dwell of 3 min at 30° C., followed by temperature ramp of 50° C. per minute, to a final temperature of 350° C. for 3 min, before baking out the system for 10 min at 450° C. and cooling.

Results:

Phenomenological Observations.

A photoreaction involving $CO_2$ proceeded in the presence of $Br_2$; other inexpensive photosensitizers that were tried, viz that were added to the liquid $CO_2$ in the fused-silica reaction vessel, but that gave no apparent photosensitized reaction when sunlight was focused on them, include titania, hemin, and candle soot. In contrast, photolysis of a ~0.5% solution of $Br_2$ in liquid $CO_2$ with focused sunlight (in the absence of polar adsorbent) gave immediate evidence of a photoreaction, with formation of a smoky-appearing product bubbling out of the illuminated spot area. (Pure liquid $CO_2$, by contrast, boils with clear bubbles lacking the smoky appearance.) Continued illumination of a ~0.5% solution of $Br_2$ in liquid $CO_2$ with tightly-focused sunlight at an ambient temperature near 0° C., for periods of 1-2 min, led to deposition of a light-gray film on the inner surface of the reaction vessel. This material was, however, not stable upon the release of pressure from the test tube, and therefore it was not analyzed.

In contrast, when silica gel was added to the photoreaction mixture, and sunlight was focused upon the silica gel saturated with the liquid phase, formation of a <1-mm³ droplet of intensely ruby-red colored material was observed, with subsequent deposition of a stable black photoproduct beginning at the center of the drop. Although photoreactions of mixtures of $Br_2$ and $CO_2$ have been studied for application in lasers (see Peterson et al., *Appl. Phys. Lett.* 27, 305-307), they have apparently not been studied in other contexts. Moreover, optical pumping of such mixtures, as low-pressure gases, was shown only to result in vibrational excitation of the $CO_2$, and no change in covalent structure was reported that could explain the observation of either a red intermediate or a black final product, as was observed in the inventor's experiments. As explained in the following paragraph, it appears that under my photolysis conditions, the red intermediate that is initially observed is most likely $Br_2C(OBr)_2$, but it might reasonably also include some $BrC=O(OBr)$ Repeated close observation of the photochemical reaction process in the presence of silica gel, or other polar adsorbents, reveals that a significant deposition rate of black material typically occurs only after a lag period of ~1-20 seconds. During this lag time, the aforementioned ruby-red viscous liquid accumulates in the region of intense solar illumination, sometimes taking on the shape of a flattened droplet on the inside of the quartz or borosilicate tube containing the sample. The ruby-red color of this material is similar to that reported for known alkyl hypobromites [Bushong, (1896-96) *Transactions of the Annual Meetings of the Kansas Academy of Science* 15, 81-82; Walling and Padwa, *J. Org. Chem.* 27, 2976-2978 (1962); Roscher and Nguyen, *J. Org. Chem.* 50, 716-717 (1985)]. Acyl hypobromites, on the other hand, have been reported to have a distinct green color [Kogure et al., *J. Mol. Struct.* 299, 105-109 (1993)]. Therefore, the ruby-red intermediate is less likely to represent bromoformyl hypobromite than the double adduct of $Br_2$ to $CO_2$, namely $Br_2C(OBr)_2$, dibromo methyl dihypobromite. Besides this and bromoformylhypobromite, all other hypothetical adducts of one or more bromine atoms to $CO_2$ lack 8-electron valence shells for at least one atom, or else contain a highly-strained 3-member ring (specifically dibromodioxirane; see below), and are thus expected to be even less stable. In addition to the red intermediate, a subsequent transient intermediate was often observed, with distinctive white luminescence.

Only with continued, intense focused solar illumination of the ruby-red material was it possible to start depositing a blackish film on the polar material, typically starting at the center (most strongly illuminated point) of the ruby red droplet; if illumination was interrupted prior to deposition of the dark product, the red intermediate visibly decayed, with a lifetime of ~10 s near 20° C., accompanied by restoration of the initial orange-colored solution. However, it was found that the presence of focused sunlight, $CO_2$, and the $Br_2$ sensitizer were insufficient by themselves to cause a visible formation rate of the black (carbonaceous) material. If additional conditions (described below) were not met, then the black material failed to form, and the ruby-red color then began dissipating immediately upon cessation or decrease in the intensity of the solar illumination. The fading of the red color typically required ~10-100 s at temperatures between 0-20° C. (with the shortest time corresponding to the highest temperature). However, the underlying silica gel did not immediately return to its starting color (which was orange-tinged due to the $Br_2$). Instead, it passed through a period of brownish coloration. This brown color was assumed to occur due to a temporary local accumulation of some other adsorbed polar material, which was nevertheless soluble in liquid-$CO_2$—and therefore subsequently (over the course of several h) dissipated through diffusion.

The additional conditions in which permanent conversion of the reddish material into a stable, immobile dark film occurred included the following:

(1) The presence of significant amounts of surface area of closely apposed polar surfaces; in the examples described herein, these were silica or glass surfaces. In these examples, "closely apposed" effectively meant that the surfaces had to start out in contact with each other, although the carbon ended up being deposited between the apposed surfaces. When a $Br_2$ solution in liquid $CO_2$ was irradiated with the solar focal point falling just beyond the inner cylindrical surface of the quartz container, but not in a region where silica or sand or glass wool or other polar surfaces were closely apposed, the reddish liquid merely accumulated upon the inner surface of the quartz tube, adjacent to the solar focal point.

(2) Sufficient focusing of the sunlight. In the case of the apparatus used in Experiments 1-3 described below, it was found that a solar spot size of at least ~0.2 mm, over which the illumination intensity was maintained at nearly the theoretical maximum achievable with a well-focused mirror having a numerical aperture of 0.6, was necessary. This is the theoretical minimum spot size that was obtained with the 0.6-numerical aperture focusing optic discussed above. (That theoretical solar spot size is determined by multiplying the angular extent of the sun in the sky, ~0.008 radians, by the focal length of the focusing optic, in this case 25 mm: 0.008×25 mm=0.2 mm.) In this case, the intensely red-colored spot often achieved a steady-state size that was just a bit smaller than this 0.2-mm theoretical solar spot size, at least when skies were clear and the off-axis paraboloid mirror was well aligned. However, for a smaller-diameter optic with similar numerical aperture, i.e. for a fused-silica asphere condenser lens with 25-mm diameter, no significant amount of red material was observed to accumulate at the position of the focal point. It was assumed that this was due to a competing diffusion of the red material away from the edges of the smaller focused spot.

(3) The presence of a UV component in the sunlight. This was deduced from a requirement for clarity of the sky (i.e. the absence of cloud or haze covering the sun), and an elevation of the sun at least ~20 degrees above the horizon. The visible light intensity obtained at the focal point of an optic is not expected to vary significantly with solar elevation, at least not until much closer to the horizon than 20 degrees. However, UV intensity varies much more, due to the changing pathlength of sunlight through the Earth's ozone layer. Therefore, the requirement for solar elevation above ~20 degrees is more likely to be due to the need for a UV photon during one or more of the multiple photochemical reactions needed to achieve the overall photolytic process of splitting $CO_2$ into its elements (see below). The experiments indicated herein were all performed at 42.9549 degrees latitude, −75.86497 degrees longitude. Near the winter solstice, when some of the experiments were performed, the low solar elevation at this latitude limited the full solar photolysis process to a short period, barely 1 h in duration, near solar noon. If the sky was not crystal-clear during this time window, no black material could be deposited, even though the bright red metastable photointermediate was present for many minutes at a time. Additionally, illumination of a sample (0.5% $Br_2$ in $CO_2$, sealed along with glass wool in a glass capillary tube and pre-cooled to 0° C.) with ~200 mW of focused blue (457-nm) output from an $Ar^+$ laser, caused the formation of a droplet of the ruby-red photoproduct. Focusing 0.5 W of 457-nm light from an $Ar^+$ laser onto a sample consisting of tightly-packed glass wool in a liquid phase consisting of 1% $Br_2$ in $CO_2$, at 0° C. resulted in the transient red photoproduct streaming slowly downward from the point of illumination, indicating that it is denser than the bulk liquid $CO_2$. Laser light of 488- or 514-nm, which are not within the absorption band of $Br_2$, was ineffective in producing the red photointermediate. Continued illumination for several minutes with 457-nm laser illumination never resulted in the formation of any stable black photoproduct; upon removal of the sample from the laser illumination, the ruby-red photoproduct apparently reverted to the starting materials, with a decay time of ~10 s.

(4) A temperature above ~0° C. Prior to commencement of solar illumination, the tube containing the sample was typically stored, or quickly re-cooled, down to a temperature of −20° C., i.e. in a standard freezer compartment of a home refrigerator. Deposition of the black film always appeared to be delayed until the temperature of the quartz tube exceeded a temperature of about 0° C. (This was checked crudely, by observing whether breathing on the tube caused transient formation of a frost, or of a liquid dew.) Furthermore, on several days when the outdoor ambient temperature was about −15° C., it was difficult or impossible to achieve deposition of the black material, even near noontime under cloudless skies, apparently because cooling by the ambient air prevented the quartz tube from ever reaching an adequate temperature. However, with the same sample, on similar days with ambient temperatures in the range 0-10° C., the deposition of black material could reliably be observed.

If all the conditions above were met, then once the noted lag period had passed, and deposition of the black material started, the deposition proceeded, and within a few seconds, the closely-apposed (touching) silica surfaces within the entire area of the imaged solar disk were typically covered, apparently uniformly, with a dark black film, that subsequently was shown to contain carbon (see below for specific results).

It should also be noted that an upper range of temperature for successful deposition of the black material has not yet been reliably observed, because of difficulties in measuring the sample temperature in ranges above ~31° C., the critical temperature for pure $CO_2$. It was easy to observe the achievement of this critical temperature, by observing loss of a meniscus between the liquid and gas phases. Several times, the formation of the black material under solar illumination was observed just as this $CO_2$ liquid-gas phase boundary was disappearing. However, continued solar illumination above the critical temperature was deemed too risky, since once this temperature was reached, there would be no further benchmarks of the internal sample temperature before the pressure could rise to several multiples of the critical pressure, possibly resulting in an explosion. The absence of additional clear warning signs of elevated pressure meant that supercriticality was used as an indicator that solar illumination should immediately cease, and the sample should be returned to the freezer for a cooling-off period.

Theoretical Rationalization.

This part of the discussion is included to provide the inventor's conjecture as to the explanation for the observed phenomena. However, it will be appreciated that this discussion is not meant to limit the scope of the invention in any way, and that on the basis of the description in this patent application, the skilled artisan will be able to carry out the claimed invention without undue experimentation.

It is well established experimentally that the enthalpy change to split carbon dioxide into its constituent elements is approximately 400 kJ/mol. This is approximately double the amount that could be provided by the absorption of 1 photon of visible light per $CO_2$ molecule. Furthermore, even in the liquid phase, $CO_2$ has no significant absorbance in the visible or UV regions of the spectrum, and would not be expected to undergo any photoreactions. The silica that may be used as the polar substrate presenting apposed surfaces also has no visible absorption. While the type E fiberglass used in some experiments described below has a UV absorbance, it is also possible to carry out the reaction just with silica gel, which is not expected to absorb significantly in the 300-400 nm range where solar UV radiation occurs.

Thus, in the photochemical process described in this disclosure, bromine appears to carry out at least two roles. First, it apparently serves as the primary photochemical absorber. Photoreactions of $Br_2$ are well known in chemistry, and include in particular the splitting of this molecule into two neutral Br atoms, upon visible light absorption. This photochemical splitting of $Br_2$ is the only plausible primary photochemical reaction that may be occurring at a significant rate at the onset of solar irradiation. However, a pair of Br atoms still does not carry enough energy, relative to the recombined diatomic molecule, to accomplish the splitting of a $CO_2$ molecule. Thus, either multiple pairs of photochemically-reacted $Br_2$ molecules must be utilized during the $CO_2$ splitting process, and/or there must be an initially formed adduct of bromine to carbon dioxide that is subsequently capable of directly absorbing additional photon(s) to complete the photolysis reaction.

Figure 2:
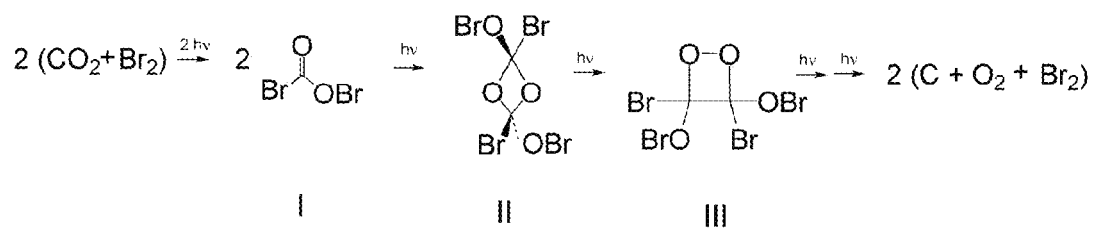
FIG. 2 shows possible intermediates and products from the reaction of molecular bromine with $CO_2$.

In order to distinguish the most likely possibilities for the identity of such an adduct, the energies of (a) a number of mono-adducts of $Br_2$ to $CO_2$, (b) a number of possible dimers of this primary adduct having the formula $C_2O_4Br_4$, and (c) the energies of these two starting molecules, were computed by using density functional theory (DFT) methods. This enabled the estimation of enthalpies of reaction to form various possible photochemical intermediates on the pathway from the starting materials to $O_2$ and C. The results are summarized in FIG. 2 and Table 1.

These computations show that it is at least in theory possible to carry out a bromine-sensitized solar photolysis reaction of $CO_2$ by using only a series of energetic jumps that are smaller than the quanta contained in visible photons.

Energies of the individual molecules were computed, and geometries were optimized to a local energy minimum, by using GAUSSIAN03W (via GAUSSVIEW 4.1), with the following keywords: opt=tight rb31yp/6-311+g(2d,2p) integral=grid=ultrafine scf=tight symm=loose. The results of these density functional theory (DFT) computations, which are presented in Table 1 below, indicate that structure I in Scheme I has an energy 207 kJ mol$^{-1}$ above ($CO_2$+$Br_2$). This is somewhat less than the 260 kJ mol$^{-1}$ available from blue (450-nm) photons. DFT computations also indicate the lowest-energy isomer of $C_2O_4Br_4$ is trans-2,4-dibromo-2,4-dihypobromo-1,3-dioxetane (II). Its energy is ~130 kJ mol$^{-1}$ above that of a pair of bromoformyl hypobromite (I) molecules. (The cis form of II is computed to be ~1 kJ mol$^{-1}$ higher in energy than trans; see Table 1.). In contrast, the next-lowest-energy $C_2O_4Br_4$ isomer, 3,4-dibromo-3,4-dihypobromo-1,2-dioxetane III, is computed to be ~400 kJ mol$^{-1}$ above two molecules of I. That is, photodimerization of I to II could be accomplished with the energy of a single visible photon, while photodimerization of I to III would require at least two such photons.

Another isomer of $C_2O_4Br_4$, tetra(hypobromyl)ethylene (($BrO)_2C$=$C(OBr)_2$), gives a computed energy ~320 kJ mol$^{-1}$ above two molecules of I, and an optimized geometry that is far from symmetrical: two of the four O—Br bonds are >2.5 Å in length, meaning that the structure is essentially two Br atoms plus di(hypobromyl)oxalate, $C_2O_4Br_2$. This isomer can thus be ruled out as the structure for the red transient photoproduct.

Table 1 shows a summary of the direct output of the GAUSSIAN computation, including, for each molecule shown, the computed energy (in Hartree units), computed dipole moment (in Debyes), angles (in degrees) and z-matrix, with distances in Å.

TABLE 1

Optimized geometries and energies of starting materials, and possible reaction intermediates.

Compound: carbon dioxide

Energy = −188.65063969    Gradient = 0.00000619    Dipole Moment = 0

| Tag | Symbol | NA | NB | NC | Bond | Angle | Dihedral | X | Y | Z |
|---|---|---|---|---|---|---|---|---|---|---|
| 1 | C | | | | | | | 0 | 0 | 0 |
| 2 | O | 1 | | | 1.160364 | | | 0 | 0 | 1.160364 |
| 3 | O | 1 | 2 | | 1.160364 | 180 | | 0 | 0 | −1.16036 |

Compound: bromine (dibromine)

Energy = −5148.27618266    Gradient = 0.00000139    Dipole Moment = 0

| Tag | Symbol | NA | NB | NC | Bond | Angle | Dihedral | X | Y | Z |
|---|---|---|---|---|---|---|---|---|---|---|
| 1 | Br | | | | | | | 0 | 0 | 1.17092 |
| 2 | Br | 1 | | | 2.341839 | | | 0 | 0 | −1.17092 |

Compound: bromoformyl hypbromite

Energy = −5336.84717185    Gradient = 0.0000039    Dipole Moment = 2.7181

| Tag | Symbol | NA | NB | NC | Bond | Angle | Dihedral | X | Y | Z |
|---|---|---|---|---|---|---|---|---|---|---|
| 1 | C | | | | | | | 0.726834 | 1.089962 | 3.6E−06 |
| 2 | O | 1 | | | 1.181529 | | | 1.401524 | 2.059913 | −8.9E−06 |
| 3 | O | 1 | 2 | | 1.348695 | 119.1934 | | −0.61536 | 1.222245 | 1.22E−05 |
| 4 | Br | 1 | 2 | 3 | 1.946329 | 122.2469 | 179.9996 | 1.485167 | −0.70256 | 5E−07 |
| 5 | Br | 3 | 1 | 2 | 1.870996 | 123.2393 | 179.9988 | −1.78946 | −0.2345 | −1.9E−06 |

Compound: trans-2,4-dibromo 2,4-dihypobromyl 1,3-dioxetane

Energy = −10673.64266857    Gradient = 0.00000308    Dipole Moment = 0

| Tag | Symbol | NA | NB | NC | Bond | Angle | Dihedral | X | Y | Z |
|---|---|---|---|---|---|---|---|---|---|---|
| 1 | O | | | | | | | 0.302471 | 0.243178 | −0.94803 |
| 2 | C | 1 | | | 1.40206 | | | −0.90732 | 0.260321 | −0.23959 |
| 3 | C | 1 | 2 | | 1.424702 | 87.1023 | | 0.907319 | −0.26032 | 0.239587 |
| 4 | O | 3 | 1 | 2 | 1.40206 | 92.89771 | 0 | −0.30247 | −0.24318 | 0.948027 |
| 5 | Br | 3 | 1 | 2 | 1.976163 | 111.9312 | 116.4011 | 1.632084 | −2.08093 | −0.01597 |
| 6 | O | 3 | 1 | 2 | 1.362451 | 115.7266 | −111.89 | 1.778848 | 0.581743 | 0.862194 |
| 7 | Br | 6 | 3 | 1 | 1.866045 | 115.1856 | −66.5546 | 3.340989 | 0.952832 | −0.08867 |
| 8 | Br | 2 | 1 | 3 | 1.976163 | 113.1454 | 115.3626 | −1.63208 | 2.080933 | 0.015966 |
| 9 | O | 2 | 1 | 3 | 1.362451 | 108.27 | −118.321 | −1.77885 | −0.58174 | −0.86219 |
| 10 | Br | 9 | 2 | 1 | 1.866045 | 115.1856 | 169.1561 | −3.34099 | −0.95283 | 0.088665 |

Compound: cis 2,4-dibromo 2,4-dihypobromyl 1,3-dioxetane

Energy = −10673.64231329    Gradient = 0.00000141    Dipole Moment = 0.7524

| Tag | Symbol | NA | NB | NC | Bond | Angle | Dihedral | X | Y | Z |
|---|---|---|---|---|---|---|---|---|---|---|
| 1 | O | | | | | | | 0.286618 | 0.057995 | −0.98414 |
| 2 | C | 1 | | | 1.402903 | | | −0.93101 | 0.05095 | −0.28738 |
| 3 | C | 1 | 2 | | 1.425504 | 87.09427 | | 0.931007 | 0.050949 | 0.287381 |
| 4 | O | 3 | 1 | 2 | 1.402903 | 92.90288 | −0.57618 | −0.28662 | 0.057994 | 0.984144 |
| 5 | Br | 2 | 1 | 3 | 1.971738 | 113.2176 | 115.5855 | −1.99765 | 1.685049 | −0.56978 |
| 6 | O | 2 | 1 | 3 | 1.362829 | 108.1613 | −117.992 | −1.59924 | −1.09175 | −0.61142 |
| 7 | Br | 6 | 2 | 1 | 1.867433 | 115.2318 | 169.4611 | −3.10365 | −1.4575 | 0.432753 |
| 8 | 0 | 3 | 1 | 2 | 1.362829 | 115.9687 | 111.2531 | 1.599243 | −1.09175 | 0.61142 |
| 9 | Br | 3 | 1 | 2 | 1.971737 | 111.6045 | −116.976 | 1.997648 | 1.685047 | 0.569782 |
| 10 | Br | 8 | 3 | 1 | 1.867433 | 115.2318 | 66.80757 | 3.103649 | −1.45749 | −0.43275 |

Compound: trans 3,4-dibromo 3,4-dihypobromyl 1,2-dioxetane

Energy = −10673.54164417    Gradient = 0.0000006    Dipole Moment = 2.7181

| Tag | Symbol | NA | NB | NC | Bond | Angle | Dihedral | X | Y | Z |
|---|---|---|---|---|---|---|---|---|---|---|
| 1 | O | | | | | | | −1.44145 | −1.16268 | 0.581639 |
| 2 | Br | 1 | | | 1.869567 | | | −1.73295 | −1.3513 | −1.2554 |
| 3 | Br | 1 | 2 | | 2.826987 | 91.54729 | | −1.66557 | 1.649936 | 0.406099 |
| 4 | O | 1 | 2 | 3 | 3.102872 | 136.4418 | −64.539 | 0.732444 | 0.108265 | 2.394569 |
| 5 | O | 4 | 1 | 2 | 1.480792 | 41.15154 | 146.1646 | −0.73243 | −0.10827 | 2.394569 |
| 6 | C | 4 | 1 | 5 | 1.411266 | 54.76235 | −149.815 | 0.78582 | 0.038216 | 0.986053 |

TABLE 1-continued

Optimized geometries and energies of starting materials, and possible reaction intermediates.

| | | | | | | | | | | |
|---|---|---|---|---|---|---|---|---|---|---|
| 7 | C | 1 | 5 | 4 | 1.363021 | 37.82003 | −59.0089 | −0.78581 | −0.03822 | 0.986059 |
| 8 | Br | 6 | 4 | 1 | 1.990022 | 110.4687 | −89.5312 | 1.665572 | −1.64994 | 0.406087 |
| 9 | O | 6 | 4 | 1 | 1.36302 | 105.865 | 147.051 | 1.441454 | 1.162678 | 0.581637 |
| 10 | Br | 9 | 6 | 4 | 1.869567 | 116.7293 | 178.0493 | 1.73294 | 1.351306 | −1.25541 |

Compound: tetra(hypobromyl)ethylene

Energy = −10673.57135491   Gradient = 0.00070159   Dipole Moment = 6.5077

| Tag | Symbol | NA | NB | NC | Bond | Angle | Dihedral | X | Y | Z |
|---|---|---|---|---|---|---|---|---|---|---|
| 1 | C | | | | | | | −0.72135 | −0.16155 | −0.0545 |
| 2 | C | 1 | | | 1.549251 | | | 0.814733 | −0.01218 | −0.18987 |
| 3 | O | 1 | 2 | | 1.203852 | 117.2874 | | −1.13005 | −1.06841 | 0.623613 |
| 4 | O | 2 | 1 | 3 | 1.200679 | 118.6574 | 91.51948 | 1.368385 | −0.5611 | −1.10299 |
| 5 | O | 2 | 1 | 3 | 1.32823 | 119.9225 | −81.4148 | 1.508655 | 0.591918 | 0.768109 |
| 6 | O | 1 | 3 | 2 | 1.324336 | 121.4011 | 174.4882 | −1.54672 | 0.608786 | −0.74674 |
| 7 | Br | 3 | 1 | 6 | 2.510789 | 117.7338 | 16.2023 | −3.47922 | −1.85952 | 0.224114 |
| 8 | Br | 4 | 2 | 1 | 2.590708 | 113.939 | −141.854 | 3.676713 | −1.56141 | −0.48432 |
| 9 | Br | 6 | 1 | 3 | 1.880678 | 117.9917 | 177.0583 | −0.81284 | 2.049811 | −1.70685 |
| 10 | Br | 5 | 2 | 1 | 1.882893 | 118.0008 | −10.2099 | 0.553557 | 1.498917 | 2.113629 |

Compound: trans-dibromo,di(bromoperoxy)ethylene

Energy = −10673.43416039   Gradient = 0.00000777   Dipole Moment = 0

| Tag | Symbol | NA | NB | NC | Bond | Angle | Dihedral | X | Y | Z |
|---|---|---|---|---|---|---|---|---|---|---|
| 1 | C | | | | | | | −0.7197 | 0.4768 | −1.0521 |
| 2 | C | 1 | | | 1.355162 | | | −1.2629 | 0.5442 | 0.1876 |
| 3 | O | 1 | 2 | | 1.430068 | 119.9988 | | 0.7011 | 0.4336 | −1.2088 |
| 4 | O | 2 | 1 | 3 | 1.429965 | 119.9991 | −179.995 | −2.6836 | 0.5873 | 0.3443 |
| 5 | O | 3 | 1 | 2 | 1.320024 | 109.4694 | −179.997 | 1.0004 | 0.3706 | −2.4929 |
| 6 | O | 4 | 2 | 1 | 1.319954 | 109.475 | −179.999 | −2.983 | 0.6504 | 1.6283 |
| 7 | Br | 6 | 4 | 2 | 1.800058 | 109.5021 | 179.9996 | −4.7713 | 0.7047 | 1.8264 |
| 8 | Br | 5 | 3 | 1 | 1.799973 | 109.5004 | 179.9996 | 2.7886 | 0.3162 | −2.6911 |
| 9 | Br | 2 | 1 | 3 | 1.910042 | 120.0016 | 0 | −0.1309 | 0.5815 | 1.7256 |
| 10 | Br | 1 | 2 | 4 | 1.909957 | 119.9995 | 0.011234 | −1.8517 | 0.4397 | −2.59 |

We propose that the metastable red photoproduct is specifically a dibromo dihypobromo dioxetane, most likely a 1,3-dioxetane (II). This species has a computed energy that exceeds that of starting materials ($CO_2$ and $Br_2$) by an amount that is ⅔ as large as the value expected if the $CO_2$ were to be decomposed into its elements. (The latter value was not computed, but was obtained from the well-known experimental value of −400 kJ mol$^{-1}$ for the combustion enthalpy of graphite.) Thus the energy required for III to be further photoreacted to its elements is (just barely) available from a single additional blue photon.

The foregoing energy analysis is intended only to indicate the thermodynamic feasibility of the interpretation given here to the observations presented. The practice of embodiments of invention itself does not require the proposed reaction scheme to be correct, let alone require the complete identification of the chemical species that are produced as end products. Skilled artisans will appreciate that they are practicing the claimed process for reducing $CO_2$ by correct identification of an end product as a stable solid material containing carbon.

Under the conditions that produced the largest amount of carbon (~1.5 mg total), this product was also determined to contain approximately 1 bromine atom per 12 carbon atoms (see Experiment #5 below). It likely also contains small amounts of oxygen and/or hydrogen. But because the end product is stable at ambient temperature and pressure, and contains carbon, it is not the starting material, carbon dioxide. Therefore, the net result of the reaction is, by necessity, a reduction in the number of $CO_2$ molecules, and therefore the sequestration of carbon away from the atmosphere. And because the end product can be combusted to re-form gaseous carbon dioxide during the combustion analysis, it must contain reduced carbon. This means that it has stored some solar energy.

Identity of the Oxidized Photoproduct(s).

As stated above, the reaction produces reduced carbon as an end product. We have not directly detected the presumptive other product of the reaction, $O_2$ gas. The amount of this gas produced, at least so far, would be expected to be a small percentage of the gaseous $CO_2$ remaining. However, there is no reasonable way to account for formation of a stable reduced carbon solid from $CO_2$, other than by the accompanying formation of $O_2$. This is because the release of reduced C from $CO_2$ requires at least one other product with an atomic ratio of O:C that is greater than the 2:1 value found in the starting material. Stated slightly differently, the formation of reduced C from $CO_2$ requires at least one other product with an increase in its oxidation state, relative to the starting materials. Other than $O_2$, there are no molecules with O:C ratios greater than 2, or that represent chemically oxidized species, that are kinetically stable near room temperature, and that could be made from the elements present in the reaction container. The most obvious other possible oxidized product molecules with O:C>2 are, like $O_2$, carbon-less and gaseous near room temperature. These include $O_3$ (ozone) and the metastable oxides of bromine. Even the most stable of these carbon-free gases ($Br_2O$) is known to decompose to form $O_2$ in the dark at temperatures above 0° C., within several minutes at most [Seppelt, 1997, *Acc. Chem. Res.* 30: 111-113].

It is impossible to rule out absolutely the formation of compounds containing all 3 fluid-phase starting elements—bromine, carbon, and oxygen—with an O:C ratio greater than 2, e.g. $C(OBr)_4$ or $C_2(OBr)_6$. However, such high-energy compounds have never been reported, and, if formed, are extremely likely to decompose spontaneously at room temperature, ultimately yielding at least some $O_2$, in any event, such compounds were not detected by mass spectrometry in our reaction products.

One final possibility is that the polar substrate, e.g. silica or alumina, present in the reaction vial might undergo an oxidation reaction when the elemental carbon is produced. However, this seems extremely unlikely, since there are no known stable oxidation states of silicon and aluminum higher than are present in silicon (IV) oxide (silica) and aluminum (III) oxide (alumina).

The O:C ratio in carbon monoxide (CO) is less than in the starting $CO_2$, and it contains no atoms with increased oxidation numbers, so a hypothetical CO product could not contribute to the requisite elemental and redox balancing. The presence of any significant concentration of $O_2$ in the gas phase means also that any CO formed would also be expected to be metastable, so CO also is unlikely to be a significant by-product of this photochemical reaction, although it also seems likely that it is produced in small quantities, i.e. far below a 1:1 stoichiometry.

Thus, according to well-understood chemical principles that are familiar to those with an ordinary understanding of the art, the indirect conclusion that elemental oxygen is formed as well as reduced carbon, is essentially inescapable.

Observations of Macroscopically Measurable Amounts of Carbon Under Seven Specific Sets of Photolysis Conditions.

Experiment #1:

In late December, a sample consisting of ~0.5 g washed quartz sand, ~0.5 g Owens-Corning type-E fiberglass ("glass wool"), 75 µl freshly distilled $Br_2$, and 3 g solid $CO_2$ were subjected to ~2-min episodes of illumination with focused sunlight. These all occurred between 11:30 and 13:00 Eastern Standard Time, when the sun was at an elevation between 20 and 25 degrees above the horizon at latitude 42.9 degrees. The ambient outdoor temperature was between −5 and 0° C. during this time period. Due to challenges in maintaining alignment of the focusing mirror, it is estimated that the actual total illumination time with well-focused sunlight was <30 min. Within this period of illumination, it was possible to generate a substantial blackened area, in excess of 10 $mm^2$ in size, within the region containing glass wool, as can be seen in FIGS. 1A and 1B.

It was also possible to produce smaller (~0.1 $mm^2$) blackened spots within the lower region of the tube that contained only quartz sand. These spots are too small to be seen in the photographs in FIGS. 1A and 1B. The spots could only be produced where individual particles of sand contacted the inner surface of the fused silica photoreaction tube, or else where two particles of sand contacted each other. Furthermore, sand with large particle sizes (~0.5 mm) did not give results as good as those obtained with more finely-divided sand. Despite repeated attempts to produce the black photoproduct on the inner surface of the fused silica photoreaction tube (i.e., where there was no sand or glass wool), to date this has not been accomplished.

These results show that a single silica surface does not serve as a useful nucleation site for the deposition of the carbon photoproduct. Instead, this nucleation requires the presence of two such surfaces in contact with each other. The extensive contact of the aligned glass-wool fibers along their lengths enables the photodeposition reaction to occur more easily than the intermittent contact points found in the comparatively larger sand particles. Thus the glass wool is used in the preferred embodiment of the invention, but substitution of quartz sand or small glass beads for the glass wool is also possible.

After illumination on December 27, the sample was stored for 3 days in a home freezer at −20° C., during which time the volume of the $CO_2$ was reduced by approximately 2 mL, or 50%. Then digital photographs of the stable black photoproduct were taken. These are the images shown in FIGS. 1A and 1B, which demonstrate the production of a good amount of black photoproduct at the specific locations where focused sunlight hit the sample.

Subsequently, the pressure inside the quartz photoreaction tube was released by loosening the cap. Excess $CO_2$ and $Br_2$ were allowed to completely evaporate over several weeks with the tube loosely capped at room temperature, during which time there was no change in the appearance of the black spot on the glass wool. This demonstrated that the black photoproduct is stable at room temperature, even when exposed to atmospheric $O_2$ and $H_2O$.

The glass wool was then removed from the quartz tube with tweezers, placed in 1.5-mL polyethylene Eppendorf centrifuge tube, tightly capped and sealed with Parafilm®, and then subjected to 1 week of digestion, at 80° C., with 4 M NaCl containing additionally 1 M NaOH, with vigorous manual agitation for several minutes each day. Within the first day of this treatment, the glass wool that was not covered by the black carbonaceous coating disintegrated into microscopically small pieces. In contrast, the black colored material remained in patches as large as ~1 mm, over the entire duration of this treatment, as well as after subsequent extensive washing with deionized water. When examined by eye and under an optical microscope, these patches clearly still contained some mats of glass fibers. Thus the chemical coating of these mats of fibers with the black colored photoproduct served to protect them from chemical attack by aqueous salt solutions. Such solutions are otherwise clearly capable of causing the mechanical weakening, and eventual breakdown, of such glass fibers.

A number of the pieces of black material were removed from the washed sample by means of tweezers, and collected into a separate 1.5-mL Eppendorf tube, where they were subjected to further washing with deionized water. The sample was pelleted in a microcentrifuge (3000×g) after each of these washes. The final pellet was dried at 80° C. for 48 h, and weighed. Its weight was 5 mg, and it formed a cohesive mass that simplified its transfer to and from a weighing boat within the Mettler analytic balance used for the mass determination.

This sample was mailed in a fresh polyethylene Eppendorf tube for C/H elemental analysis by Midwest Microlabs (Indianapolis, Ind.). Two independent determinations were made, with the following results: % C, 4.70/4.98; % H, 1.55/1.53; % Ash, 81.0%. These results indicate that the 5-mg sample contained mostly the original carbon-free glass wool, but also contained 0.24 mg of carbon. Based on the blackened color produced upon the fibers, it was concluded that the carbon in this product had most likely been produced by photochemical reduction of the original $CO_2$. There was no evidence of any roughening or other type of loss of polyethylene from the inner surface of the Eppendorf tube, which was the only other possible source of organic carbon material. The alkaline solution used to digest the glass fibers was, in theory, capable of absorbing $CO_2$ from the atmosphere as sodium carbonate, but the tight capping of the tube during the digestion process makes this degree of carbonate absorption and formation unlikely.

The results of this experiment point to the utility of the described photoreaction process in producing a new hybrid material, consisting of glass fibers embedded in a carbonaceous solid. This hybrid material has improved chemical resistance as well as good resistance to mechanical disruption.

Experiment #2:

In late February, a sample consisting of 0.5 g silica gel (Sorbent Technologies, 40-70 micron particle size), 1 g of 3-mm glass spheres (marketed as bacterial sample spreaders for culture plates, but never used for this purpose) 20 µl freshly distilled $Br_2$, and 3 g solid $CO_2$ were subjected to focused sunlight under cloudless, but slightly hazy skies on both days. On the first day, periods of illumination began at 11:30 EST, and production of black photoproduct continued intermittently until 2:30 p.m. On the second day, illumination began at 11 a.m. EST and continued intermittently until 1 p.m. During the indicated hours, the sun was at an elevation between 31 and 42 degrees above the horizon at latitude 42.9 degrees. The ambient outdoor temperature was between 0° C. and 15° C. during these time periods. In between periods of illumination, the sample container was removed from its clamp, and subjected to ~30 s of gentle shaking, to disrupt the spots where blackened photoproduct had formed, and release this photoproduct as tiny black fibrous specks within the silica gel, which was otherwise orange-colored due to adsorbed $Br_2$.

Under intense solar illumination, the sample reached the critical temperature every 5-10 minutes, requiring return to the home freezer for 5-10 minutes of cooling. Due to challenges in maintaining alignment of the focusing mirror, and in keeping the sample cooled, it is estimated that the actual total illumination time with well-focused sunlight was <1 h total.

After illumination was completed, the sample was returned to the freezer for 14 h, and then checked to see that the visual appearance had not changed upon storage. Black fibers and particles were still clearly visible among the particles of silica gel, and there remained 3-5 small (~0.1-0.5 mm) black spots on the walls of the silica photoreaction vessel, which gentle agitation of the silica gel and glass spheres for 5-10 min still could not dislodge.

The pressure was then released from the sample by slowly unscrewing the GL14 closure. The sample was allowed to remain at room temperature for 2 h, then the remaining solids were transferred initially to a glassine weighing paper, then to a 1.5-mL eppendorf tube. During this process, the tip of a stainless steel spatula was used to dislodge as much as possible of the blackened material still adhering to the inner wall of the silica photoreaction tube. By this sequential transfer process, it was possible to remove the glass spheres, leaving just the silica gel with small black particles spread throughout it.

1 mL of 10 M NaOH was added to the solid powdery sample; the cap of the Eppendorf tube was closed and sealed with Parafilm, and the sample was allowed to digest for 24 h at 80° C. This was sufficient time to permit complete dissolution of the silica gel into the alkaline solution, making a fairly concentrated sodium silicate solution. The black material appeared to be completely liberated from the silica gel, and was dispersed throughout the solution as a flocculent fibrous solid. The Eppendorf tube was centrifuged in a microcentrifuge (5 min, 3000×g). While a small portion of the black material sedimented to the bottom, most remained floating on top, with an additional portion dispersed throughout the sodium silicate solution.

Figure 6:
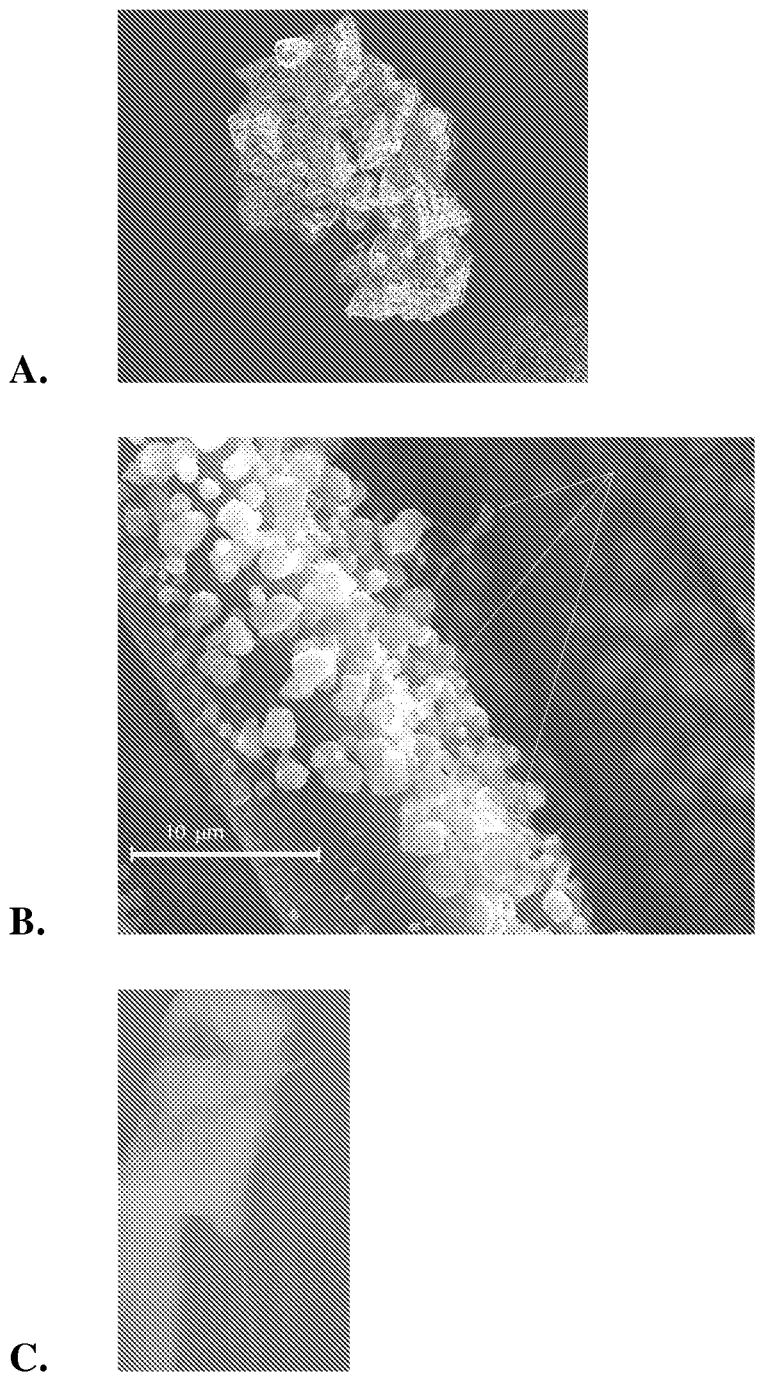
FIGS. 6A and 6B are electron micrographs.
FIG. 6C is a scanning electron micrograph, of products of the reaction of molecular bromine and $CO_2$ in accordance with embodiments of the invention.

Addition of 0.5 mL deionized water, followed by re-centrifugation, sufficed to cause all of the black material to sediment into a tightly packed pellet at the bottom of the Eppendorf tube. The sodium silicate solution was removed, then the black pellet was washed 5 times, each by adding 1-mL portions of deionized water, with vortexing, followed by re-centrifugation and removal of the supernatant. The pellet was then air-dried 30 min at 80° C., followed by 24 h at 40° C. Its mass was determined to be 0.3 mg. This was not sufficient for elemental C determination by Midwest Microlabs. However, its identification as elemental carbon, of either amorphous or microfiber (carbon nanotube) composition, is supported by a number of observations, including: the flocculent appearance of the material prior to centrifugation; its resistance to degradation by concentrated sodium hydroxide; its formation of a tightly-packed jet-black pellet; and its ability (at least in part) to float on top of an aqueous sodium silicate solution, while being also partially sedimented. The black coloration and solidity of the sample suggest that it is not principally a bromocarbon, at least not any low-molecular-weight bromocarbon. Its fibrous appearance, especially when first liberated from the silica gel, suggest that it is more likely to be carbon than silicon, since elemental silicon generally does not form fibrous structures. The moderately high density of the sample, ranging around the specific gravity of a 30% solution of sodium silicate, suggested that it might include a substantial fraction of well-ordered carbon nanotubes. However, electron microscopy of this material (FIGS. 6A, 6C) shows evidence principally of amorphous particulate clusters, with only a small portion appearing under TEM (FIG. 6C) as if it might possibly include some nanotubes. In particular, scanning electron micrography (SEM) of the carbonaceous product on the glass-wool polar substrate indicated mainly amorphous islands ~1 µm in dimension, with a few longer tubular structures admixed (see FIGS. 6A and 6B. FIG. 6A shows a scanning electron micrograph of a typical large particle obtained from the bromine-sensitized solar photolysis of $CO_2$, followed by alkaline digestion of the silica gel used as a polar adsorbent. The total width of the image in FIG. 6A is 2048 pixels=268 µm; it was obtained using 15.0 kV, 200× magnification, 0 tilt, and 0.313 µm per pixel. The 3 lines in FIG. 6B point to examples of tubular structures, spread among the predominantly amorphous particles deposited on the fiber surfaces. This image was obtained using 30.0 kV, 3700× magnification, 0 tilt, and 0.034 µm per pixel.). The alkaline digestion process, when applied to a sample prepared using silica gel as the polar substrate, apparently selected for the largest particles in the sample, yielding ~100 µm clumps composed of 10-µm particles.

Figure 3:
FIG. 3 is a photograph of a reaction vessel after reaction of molecular bromine and $CO_2$ in accordance with an embodiment of the invention.

Experiment #3:

In mid-April, a sample consisting of 0.35-g aluminum oxide bulk chromatography adsorbent at the bottom, 5 µl $Br_2$, and 3 g solid $CO_2$ were subjected to repeated episodes of illumination with focused sunlight, each 2-5 min in duration. These all occurred between 11:00 and 14:00 Eastern Daylight Time on the two successive days, when the sun was at an elevation between 45 and 56 degrees above the horizon. The ambient outdoor temperature was between 10° and 20° C. during this time period. As shown in FIG. 3, a total of some 60 spots of blackened material were produced. (The orange-colored liquid phase seen in FIG. 3 is 0.5% $Br_2$ in $CO_2$; separate 1-mm-sized black spots on the powdered-alumina bed represent distinct 20-s intervals of illumination spread over 2 successive midday periods, with the sample re-cooled to −20° C. and re-positioned in between each interval. The 90° off-axis paraboloid mirror is visible at the top of the photograph.) Subsequently, the pressure was released and the sample was allowed to dry. An attempt was made to dissolve the alumina in the sample by treating with 10 M NaOH at 80° C. for 1 week. However, the sample never significantly dissolved, and as a result, no elemental analysis was undertaken.

Experiment #4:

In late April, a sample consisting of 0.25 g powdered titanium dioxide (titania; Degussa P25) at the bottom, 10 µl $Br_2$, and 3 g solid $CO_2$ were subjected to three separate episodes of illumination with focused sunlight, each 2-5 min in duration. These all occurred between 10:00 and 10:15 Eastern Daylight Time, when the sun was at an elevation between 45 and 56 degrees above the horizon. The ambient outdoor temperature was between 10° and 20° C. during this time period. A total of 3 spots of blackened material were produced, each similar in size and appearance to those that had previously been produced with alumina (see Experiment #3). Subsequently, the pressure was released and the sample was allowed to dry. An attempt was made to dissolve the alumina in the sample by treating with 10 M NaOH at 80° C. for 1 week. However, the sample never significantly dissolved, and as a result, no elemental analysis was undertaken.

Figure 4:
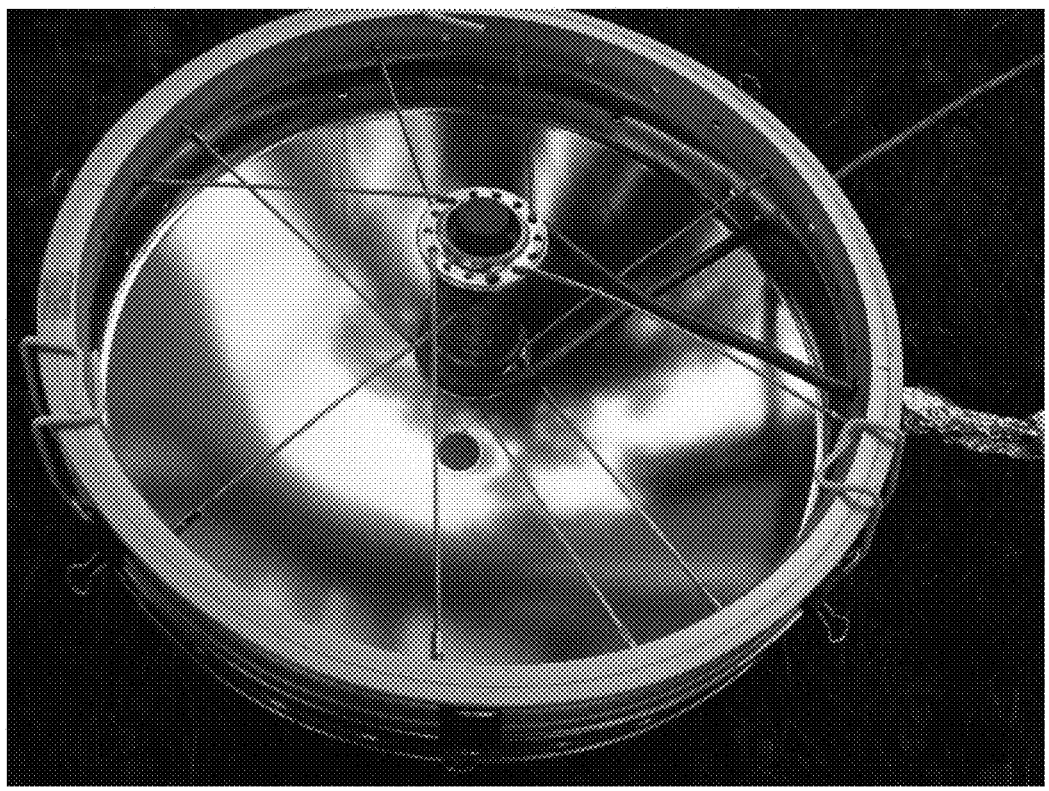
FIG. 4 is a photograph of a reactor in accordance with an embodiment of the invention.

Experiment #5:

In mid-September, 0.1 g Owens-Corning type-E fiberglass ("glass wool") tied into several knots, 4 g solid $CO_2$, and 10 µl $Br_2$ (0.016 g), were sequentially placed in a 6-mL-capacity borosilicate tube. This reaction vessel had been custom-fabricated in the preceding weeks, from a ChemGlass borosilicate GL14 threaded tube and ⅝" medium-wall borosilicate tubing, with a constriction at the joint to provide greater strength. After capping with a ChemGlass GL14 cap and storage for several h on solid $CO_2$ to allow stabilization and transportation of the sample, it was placed in the 12-inch photoreactor apparatus as shown in FIGS. 4 and 7A-B, which was cooled by pumping the liquid from an ice-brine mixture through its cooling coils (using a peristaltic pump with a flow rate of ~50 mL/min). The sample, in the bottom of the glass reaction vessel snugly held in the center of the bicycle hub, was subjected to 20 s of illumination with focused sunlight. The illumination occurred at 12:00 Eastern Daylight Time, when the sun was at an elevation 49 degrees above the horizon. The ambient outdoor temperature was approximately 20° C. during this time period. After the first 20-s period of illumination, only the ruby-red photoproduct was visible by examination with an inspection mirror held below the bottom of the tube. During the second period of illumination, this pre-formed red material, which remained at the bottom of the liquid phase and covered the glass wool almost completely, immediately began to deposit a dark black solid film upon the glass wool. After the second 20-s period of illumination, a tiny crack was visible in the borosilicate glass. Thus, after allowing only a 1-min delay to allow the sample to cool and thermally equilibrate a bit before removing it from the metal hub, the GL14 cap was quickly loosened in order to avert explosion of the glass reaction vessel.

Subsequently this sample, still in the photoreaction tube, was dried in an 80° C. heating block for 3 days. The glass wool plug was removed carefully, along with as much as possible of the black material that initially remained attached to the borosilicate glass tube itself, rather than to the glass wool. The blackened region of the glass wool was cut away from the rest with clean stainless-steel scissors, combined with the black material that had been removed from the surface of the glass tube, and then pulverized. A total of 41 mg of the pulverized glass sample, now a dark gray due to the mix of glass fibers and deposited black material, was placed in a glass vial and sent to Columbia Analytical Laboratories in Tuscon Ariz. A 15-mg control sample of glass wool that had been similarly treated (by heating in a similar borosilicate tube to 80° C. for several days, then pulverizing) was also sent.

The results of dual combustion analyses showed that the illuminated sample contained 4.5% C (4.69%, 4.36%), while the unilluminated control sample contained 0.6% C (0.44%, 0.72%). The bromine-sensitized solar photolysis therefore produced at least 1.6 mg (3.9% of 41 mg) of reduced carbon from $CO_2$, by means of at most 40 s worth of solar illumination captured by the 12-inch-diameter reflector. The overall efficiency of solar energy storage can be computed from this result. The approximate area of solar collection was 0.07 $m^2$ (taking into account some occlusion of the reflector by the hub and spokes); the time of collection was 40 s; and the solar constant is 1366 $W/m^2$. The total amount of solar energy collected was thus the product of these values, or 3.8 kJ. The amount of energy stored in the 1.6 mg of reduced carbon (0.13 mmol) was 0.00013 mol×400 kJ $mol^{-1}$, or 0.052 kJ. The overall efficiency of energy storage was thus 0.052/3.8, or about 1.3%. Although this is much lower than the values achieved for typical silicon solar cells, it is roughly comparable to plant-based photosynthesis.

Most important, this 1.3% efficiency is a non-optimized value that could likely be improved by an order of magnitude, or even more, with very minor modifications. For example, it is clear from observations that the bromine-sensitized process described herein has a rate with a very strong (supralinear) dependence on solar intensity. However, the 12-inch reflector that was used for this experiment did not produce nearly the maximum solar intensity that is possible for a reflector its size and focal length. For the 3 inch (=75 mm) focal length of this reflector, the predicted size of the focused image of the sun, which has an angular size of 0.008 radians in the sky, is 0.008 radians×75 mm, or 0.6 mm. However, this was a low-polish reflector that scattered considerable light, and produced a fuzzy image of the sun, spread out over an area of the glass wool that far exceeded 0.6 mm, indeed closer to 6 mm. Thus, the solar intensity was less than ¹⁄₁₀₀ of what might be achieved with an optimized optical system for focusing the sunlight at its tightest.

The calculation of 1.3% energy conversion efficiency was based on the assumption that the carbon produced had an enthalpy storage equivalent to that of graphite. However, the chemical state of the carbon in the product has not actually been fully elucidated. The product likely contained some bromine chemically bonded to the carbon (see next paragraph). However, this would not likely introduce any significant overestimate of the energy storage, since the enthalpy of formation of bromocarbon compounds (from graphite and $Br_2$) is always small, but positive. Instead, the biggest error that the assumption of a graphite product might have produced, would be if the product actually still contained a significant amount of oxygen chemically bonded to the carbon. This would decrease the amount of energy that was actually stored.

This experiment (#5) produced a quantity of product large enough for a reliable measurement of the relative amounts of bromine and carbon in the product. Bromine elemental analysis showed that this sample contained approximately 2.1% bromine (1.80% and 2.50% in repeat analyses), or a bit more than half of the 3.9% carbon content by weight. The observed C/Br weight ratio of 1.9 corresponds, however, to a molar ratio greater than 12. That is, the product molecules have, on average, only one bromine atom incorporated for every 12 carbon atoms. This result suggests that the bromine acts photocatalytically, i.e. that each $Br_2$ molecule in the reaction volume can carry out reduction of multiple $CO_2$ molecules. However, this is not a complete proof, because the yield of C (0.13 mmol) was still not quite as high as the total amount of $Br_2$ (5 μl, or 16 mg, or 0.2 mmol) in the initial reaction mixture, and furthermore no effort was made to determine the amount of molecular $Br_2$ recoverable after the photochemical reaction had occurred.

In any case, the yield of reduced carbon per sensitizer molecule, in excess of 8 mmol of reduced carbon per gram of $Br_2$ photosensitizer, is already 8 times what was reported for CoPc-sensitized $TiO_2$ [Liu et al., 2007].

Even more impressive is the rate of reaction achieved per gram of photocatalyst, since 0.13 mmol of product was formed by using just 16 mg of $Br_2$ for under 1 minute, even including a 20-s period of "dark time" in the middle of the reaction. This gives an (extrapolated) rate of product formation of nearly 0.5 mol of reduced carbon per hour, per gram of $Br_2$, or over 2000 times the specific rate of product formation reported for a dye-sensitized titania system [Woolerton et al., 2010]. This calculation assumes that the bromine-sensitized photolysis reaction is indeed photocatalytic, so that the $Br_2$ molecules can be re-used many times per hour.

In energy terms, the rate of energy storage achieved was already about 1 Watt per 16 mg of $Br_2$, or in excess of 80 watts per gram of $Br_2$. This is likewise an impressive achievement, especially when the low cost of $Br_2$ is considered (approximately \$1.50 per g in bulk). The cost of the requisite polar adsorbent for the reaction (e.g. fiberglass) is comparable to this, or even smaller. These figures suggest that the principal cost of producing energy with this process will be in other areas, including the cost of focusing the light; in compressing and cooling the reaction mixture; and in purifying or otherwise processing the initial products, including recycling of the unused ($CO_2$) reactant and photosensitizer materials ($Br_2$ and polar adsorbent).

To date, we have not been able to determine the O content of the stable end product, in this or any other experiments, due to an inability to separate it from the polar substrate on which it formed. The best separation was obtained when the reaction was carried out using pure silica materials for the polar substrate. Either silica gel or quartz wool used in this manner could be largely digested and dissolved by treatment for 1-3 days in 10 M NaOH at 80° C., followed by extensive washes of the black residue in water, with centrifugations in between. However, even this extensively-digested material gave at most 12% carbon upon combustion analysis, suggesting that the carbonaceous product was capable of protecting a significant portion of the silica substrate from chemical attack by alkali.

Experiment #6:

In mid-November, 0.1 g quartz wool was stuffed tightly into the bottom of a 6-mL-capacity custom-made borosilicate tube (of similar manufacture to that used in experiment #5), and dried at 80° C. under a stream of dry air for 1 h. At 11:30, 10 μL of $Br_2$ was added, and then, within 1 min, 0.05 g solid $CO_2$. (The solid $CO_2$ was a single compact roughly spherical chunk that fit through the 4-mm-diameter neck of the borosilicate reaction flask. Its mass was estimated based on previous rapid measurements, in a laboratory setting, of the masses of similar compact chunks of solid $CO_2$ that could be fit through the neck of this same reaction vial). Within seconds after adding the solid $CO_2$, the tube was tightly capped with a ChemGlass GL14 closure with PTFE lining. This sample was quickly placed into the 12-inch photoreactor apparatus shown in FIG. 4 (without any of the external cooling lines attached). The sample and parabolic collector were then immediately aligned with the sun, by using an inspection mirror to maximize the intensity of the light on the quartz wool at the bottom of the tube, and the sample was subjected to 20 s of illumination. The time was 11:35 a.m., corresponding to a solar elevation of 48 degrees above the horizon.

The overall density of $CO_2$ in the container (about 0.05 g in 6 mL, or under 10 g/L) was too low to support the formation of a pure liquid phase of $CO_2$. By comparison, the density of pure gaseous $CO_2$ at 0° C. and 1 atmosphere is 2 g/L, so this density corresponded to a pressure of under 5 bar at room temperature, and under 4 bar at the melting temperature of −78° C. This is lower than the triple-point pressure of 5.1 bar, and therefore this concentration of $CO_2$ could not sustain the formation of a liquid phase. Therefore, instead of melting, the solid $CO_2$ sublimated directly under the heating provided by the solar illumination, with only a small portion of it going into the liquid $Br_2$ phase.

Nevertheless, it was possible to rapidly produce a substantial quantity of the ruby-red intermediate, and then the black photoproduct, and to visualize this process in real time by use of a small inspection mirror placed near the apex of the paraboloid reflector. The black photoproduct remained stable after subsequent release of pressure and then drying (room temperature) for 6 days, before taking the photograph shown in FIG. 5.

Similar experiments that were attempted with a waiting time between addition of the solid $CO_2$ and solar illumination, to allow the tube to come to thermal equilibrium at an ambient temperature near 20° C., did not result in the apparent formation of the stable black photoproduct. The simplest way to account for the different behavior is that the sublimation of the solid $CO_2$ during illumination provided a cooling effect on the quartz wool and liquid $Br_2$ phase, that kept their temperature in the optimal range for the photoreaction to take place.

An important conclusion from such experiments is that use of $CO_2$ that is gaseous, rather than liquid, does not absolutely prevent the desired photoreaction from taking place. However, the presence of a substantial liquid $CO_2$ phase makes it easier to keep the reaction volume cooled to an optimal temperature between 0° and 20° C., because refluxing of the boiling liquid phase allows rapid heat exchange with the upper portions of the reaction tube that are being cooled by contact with air and with the sample holder. Without such refluxing, the bottom portion of the reaction vial has only much slower conductive and convective heat exchange with the large ambient-temperature mass of the reaction apparatus, and can heat up much too quickly to sustain the desired photolysis reaction. However, if an alternate method of cooling is applied, that keeps the illuminated liquid $Br_2$ phase in the optimal temperature range, then the reaction can proceed at pressures below 100 psi. This is a much safer and more easily sustainable pressure for widespread use, than the 700-1100 psi range required for maintaining a liquid phase of $CO_2$ near ambient temperatures.

Figure 5:
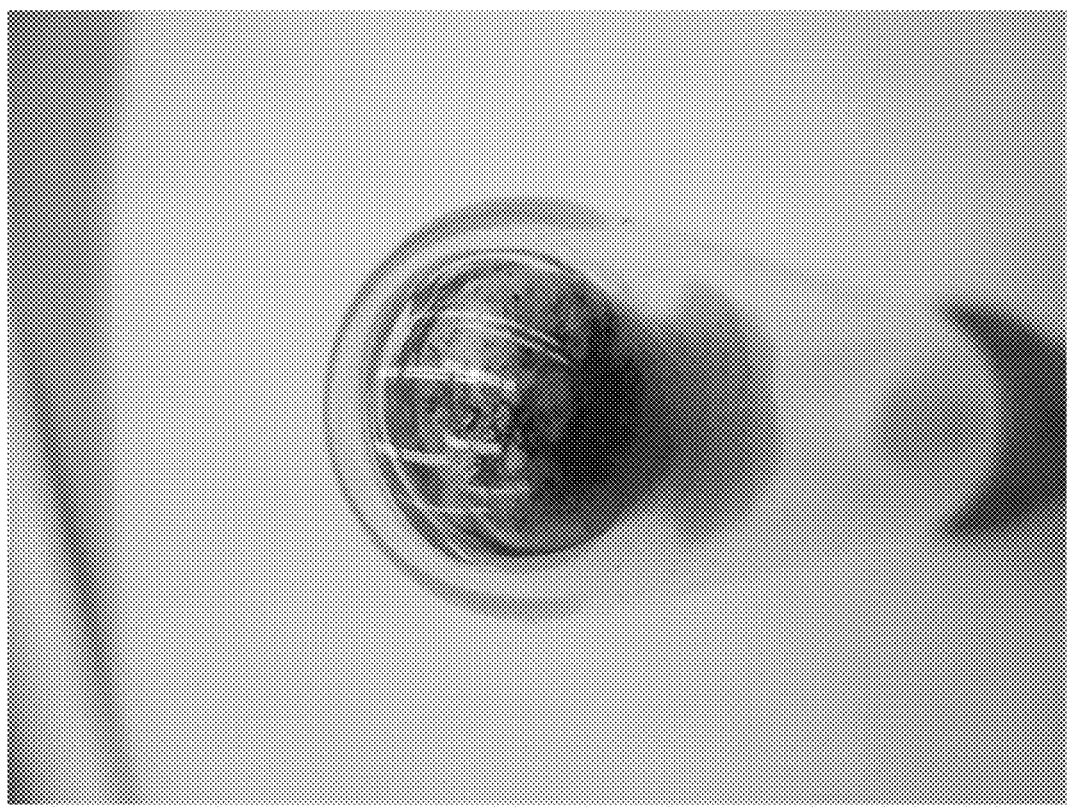
FIG. 5 is a photograph of a reaction vessel after reaction of molecular bromine and $CO_2$ in accordance with an embodiment of the invention.

After taking the photograph in FIG. 5, the quartz wool was removed from the reaction vessel, and the blackened regions were cut away from a control sample, consisting of the remainder of the quartz wool that was mostly unreacted. The blackened and control samples were heated for 24 h at 75° C. in order to allow volatile materials to evaporate, each with a small (~3 cm) piece of fresh Kimwipe® stuffed into the top of the drying tube in order to collect any less-volatile materials that might easily re-condense. The tube with the blackened quartz wool did show the presence of a brownish material on the Kimwipe®. Subsequent extraction of this piece of Kimwipe® with benzene, followed by GC-mass spec, did show the presence of some high-MW substances, such as a distinct band with a mass/charge ratio of 604. This band showed no evidence for the isotopomer distribution characteristic of bromine, i.e it did not show a sequence of bands separated by 2 amu. Therefore, it seems most likely that this band might have corresponded to a species with nearly 50 carbon atoms, along with some hydrogens and/or oxygen atoms.

The blackened quartz wool and control quartz wool samples were pulverized, yielding 59-mg and 47.5-mg samples respectively, which were then sent to Columbia Analytical for elemental analysis. The results of combustion analysis (two per sample) showed that the blackened sample contained 1.00% carbon (measurements of 0.98% and 1.01%), whereas the control sample contained 0.75% carbon (measurements of 0.77% and 0.74%). It should be noted that this control sample had higher carbon content than the glass-wool samples of experiment #5 above, probably indicating an imperfect ability to define a region of the quartz-wool sample that had been in the same reaction container but did not undergo any carbon deposition. Even assuming that only the 0.25% carbon content difference was attributable to the bromine-sensitized solar photolysis, this reaction resulting in the deposition of at least 0.15 mg of reduced carbon during the 20 s of illumination, or a rate of 0.6 micromoles of carbon per second. This is 3-4 times lower than was achieved under the more optimal conditions of experiment #5. This can reasonably be attributed to the lower concentration of $CO_2$ in the reaction vial. Nevertheless, this experiment and subsequent combustion analysis establishes that even in the absence of a liquid $CO_2$ phase, and at an overall pressure below 100 psi, the bromine-sensitized solar photolysis reaction can produce reduced carbon at a significant rate.

In addition to the carbon analysis cited in the previous paragraph, Columbia Analytical was able to perform bromine analysis on these same samples. The results were 0.65% bromine for the blackened quartz sample (0.80% and 0.50% for the two individual measurements), and 0.35% bromine for the control sample (0.30% and 0.40% for the two individual measurements). Taking the difference, 0.3%, as most representative of the amount of bromine attributable to the carbonaceous deposit, the ratio of carbon to bromine deposited was 1%:0.3% or about 3:1. Given the relatively low level of accuracy of the analysis, this ratio is close to the 2:1 ratio observed in experiment #5 above, and once again indicates that the C:Br atomic ratio in the deposited material was likely greater than 10. This supports the prior conclusion that the $Br_2$ could have been acting photocatalytically, with each $Br_2$ molecule sensitizing the photolysis of a good number (>10) of $CO_2$ molecules.

Experiment No. 7:

Mass spectral measurements of the transient red photoproduct formed in the initial phase of photoreaction of $Br_2$ with $CO_2$ was done without a programmed temperature ramp. The sample was freshly prepared immediately prior to the run, by packing ~0.01 g glass wool into the bottom of a 1-mL Pierce ReactiVial, then adding 5-10 nl freshly-distilled $Br_2$, and ~0.5 g dry ice, capping it tightly with a solid screwcap and a PTFE-laminated silicone liner, and (within seconds) exposing it to the focused sunlight from a 15-cm-diameter paraboloid mirror. (This was obtained from an after-market truck headlight, Rally Model 3125, purchased at a local auto parts store). The solar illumination was performed at N 43.0344° N latitude, 76.1376° W longitude, in a field just outside the laboratory building where the mass spectrometer is located. After ~30 s of illumination with focused sunlight, it was possible to visualize, with a small inspection mirror, that the dark-red transient photoproduct had collected on the glass wool at the bottom of the ReactiVial. This sample was cold-trapped by rapid release of $CO_2$ pressure, causing evaporation within ~1 s of the remaining 1-2 mL of liquid $CO_2$; followed by storage of the cold sample on dry ice for several minutes while it was brought indoors to the mass spectrometer. The solids probe had been pre-cooled to 0° C. A few strands of glass wool from the reaction vial, still at dry-ice temperature, were transferred to the probe by using pre-cooled steel tweezers. Then the probe was inserted into the mass spectrometer, and the measurement was begun, all within ~10 s of the sample transfer. Within several seconds, the probe warmed up to the lowest temperature setting possible (30° C.), and remained at that temperature throughout the run.

Mass spectrometry of the condensed-phase products gave no indication of formation of elemental carbon, e.g. fullerenes, with m/z at some multiple of 12. Small amounts of volatile perbrominated hydrocarbons were likely formed, e.g. $C_2Br_4$ as indicated by a set of m/z peaks at 340, 342, 344, 346, and 348. Additional less-volatile non-brominated products were also formed; these exhibited a characteristic set of m/z peaks at 217, 183, 176, 91, 86, and 65 that were detected only when the mass spec solids probe reached ~350° C. Our observations do not yet permit identification of the corresponding chemical formula (s).

Figure 8:
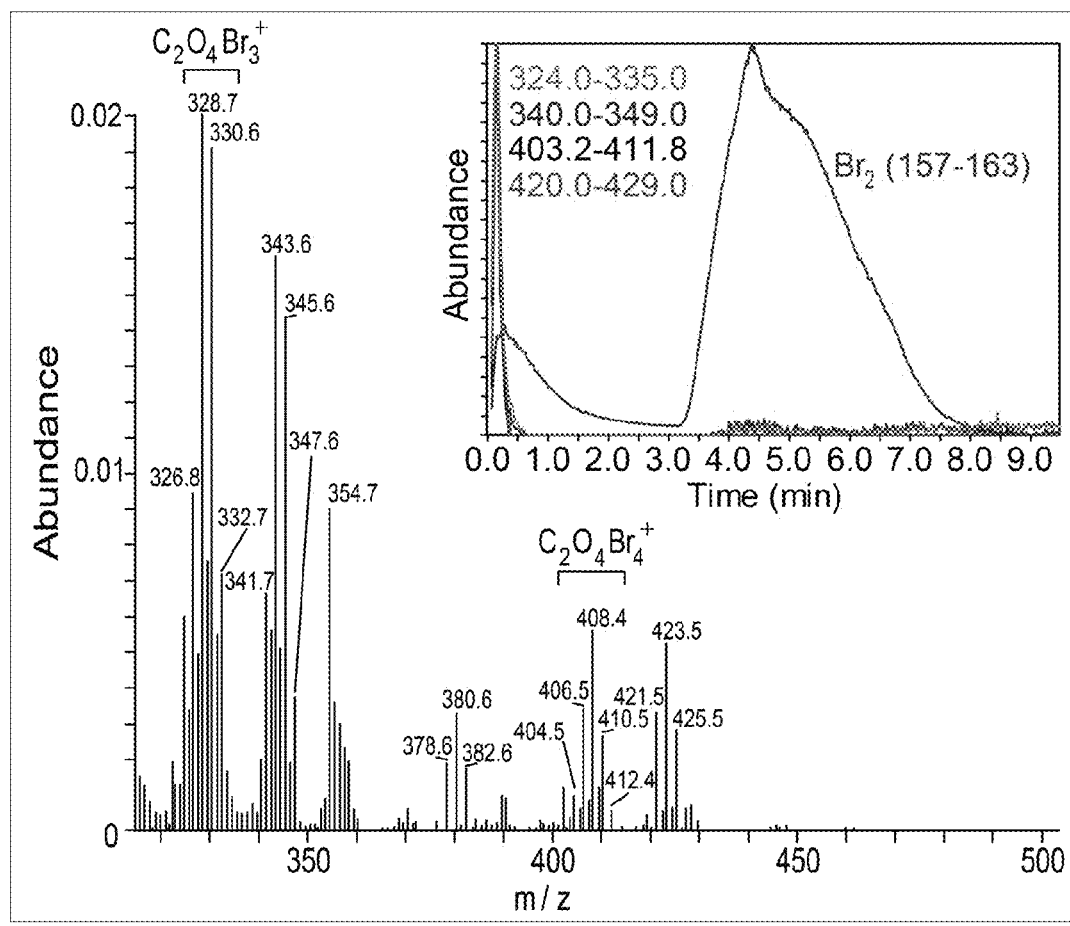
FIG. 8 shows the mass spectrum from the metastable photoproduct(s) of $CO_2+Br_2$.

Mass spectrometry of the cold-trapped red species yielded m/z peaks at 406, 408, 410, 412 and 414, in the natural-abundance isotope ratio expected for a tetrabromo species, specifically for a molecular ion with the formula $C_2O_4Br_4^+$ (see FIG. 8, which shows the mass spectrum from the metastable photoproduct(s) of $CO_2+Br_2$, measured during the first 50 s after transferring the cold-trapped reaction products into the mass spectrometer. The y-axis is normalized to the m/z peak at 160 from $(^{79}Br^{81}Br)^+$, the molecular ion of the major isotopomer of residual $Br_2$. The inset in FIG. 8 shows a comparison of four nearly superimposable time courses of detected ions (integrated ranges of 324-335, 340-349, 403-412, and 420-429) with the much different time course of $Br_2$ at m/z=158-162. Each time course was re-scaled by normalizing to its maximum value during the 9-min time of measurement.). These 5 peaks all decayed rapidly, within ~40 s, much faster than the residual $Br_2$ reactant (see the inset in FIG. 8). Additional peaks that decayed on the same time scale corresponded the same species with a methyl group (15 mass units) added, possibly arising due to a small methane contaminant in the dry ice used for the photoreaction. Other prominent sets of peaks in FIG. 8, centered near 330 and 345, correspond respectively to the species centered near 410 and 425, each minus a Br atom. No m/z peaks were observed corresponding to direct adducts of $Br_2$ to a single $CO_2$ molecule, e.g. $CO_2Br_2$ (m/z=204) or $CO_2Br_4$ (m/z=364).

It is nevertheless reasonable that $CO_2Br_2$ should be the primary photoproduct of $Br_2$ in $CO_2$ solution. This hypothesis is supported by the stability of the fluorine analog of I, fluoroformyl hypofluorite, although the latter has been produced only by photochemical reaction of $F_2$ with bis(fluoroformyl) peroxide, rather than with $CO_2$ (Argüello et al., Inorg. Chem. 34, 603-606 (1995)). If trapped at a polar surface in high concentration, I might well be expected to photodimerize to a kinetically more stable $C_2O_4Br_4$ species (II or III), as suggested in FIG. 2.

Figure 9A:
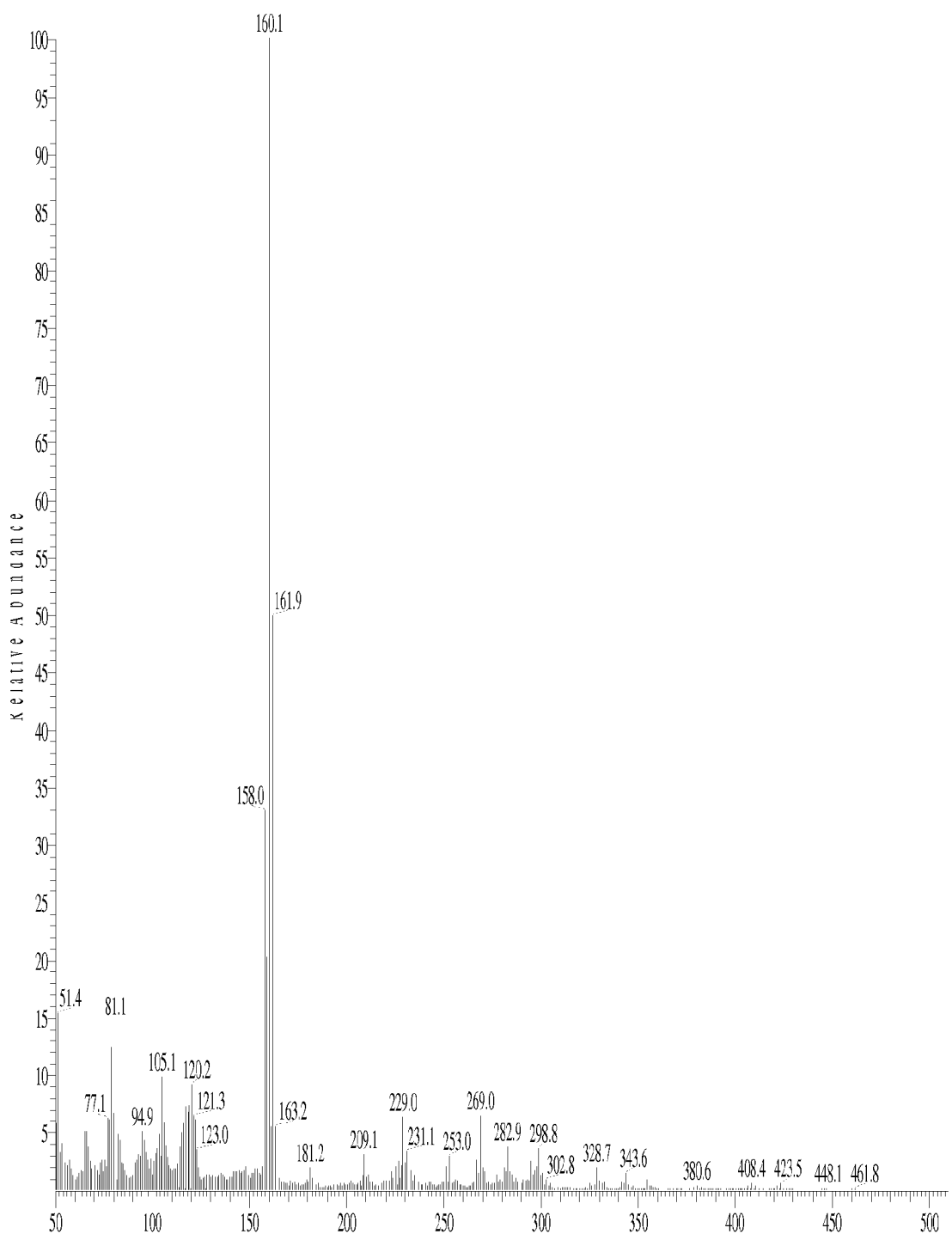
FIGS. 9A and 9B are mass spectra.
Figure 9B:
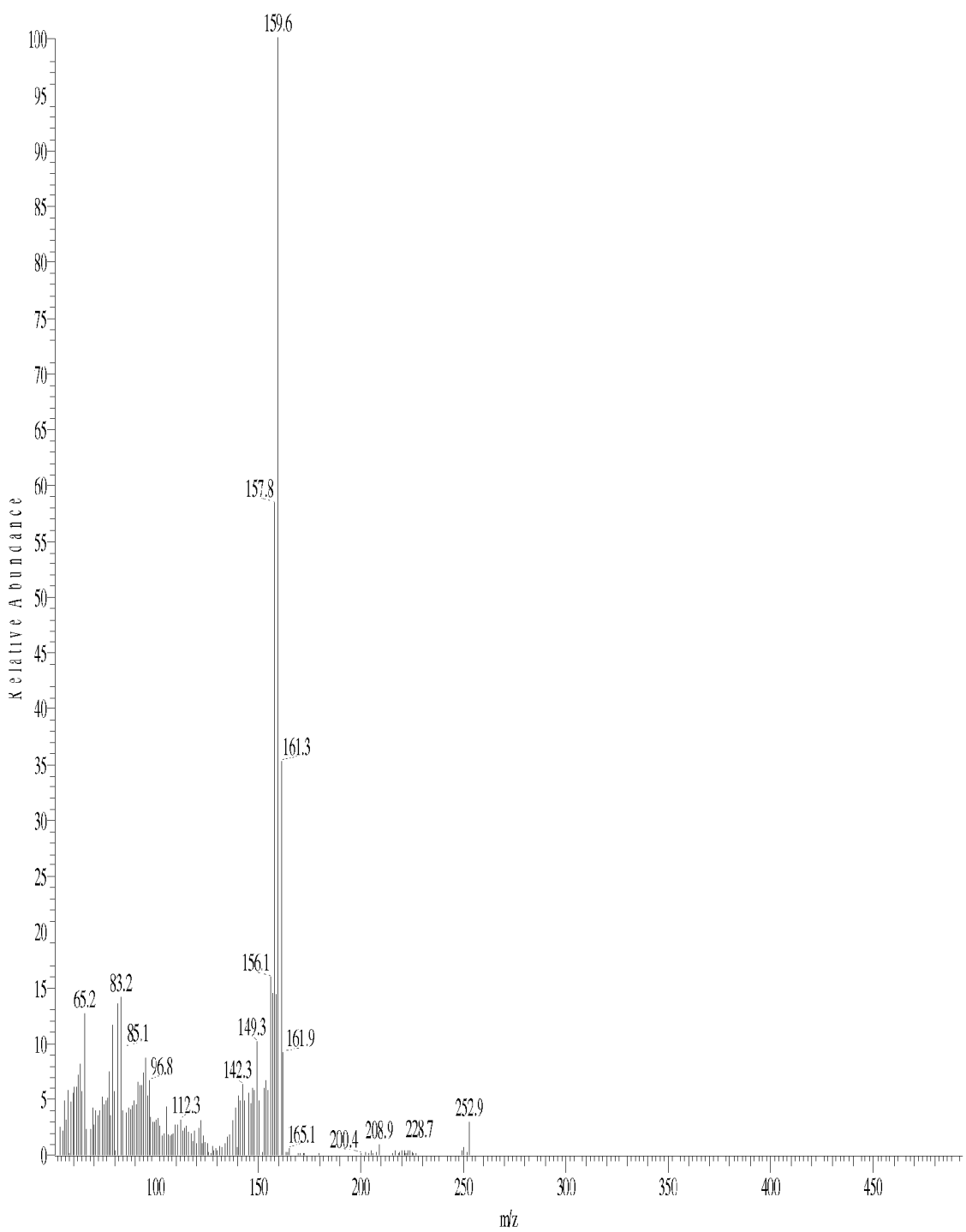

FIGS. 9A and 9B are mass spectra. FIG. 9A shows the full range of the mass spectrum shown in FIG. 8, showing the relative size of the small peaks above 300, compared to the large peaks at 158, 160, and 162 due to the 3 major isotopomers of the molecular ion of $Br_2$. Isolated Br atoms were also detected at m/z=79 and 81. FIG. 9B presents control data obtained from a sample treated identically, but never exposed to sunlight.

Figure 10A:
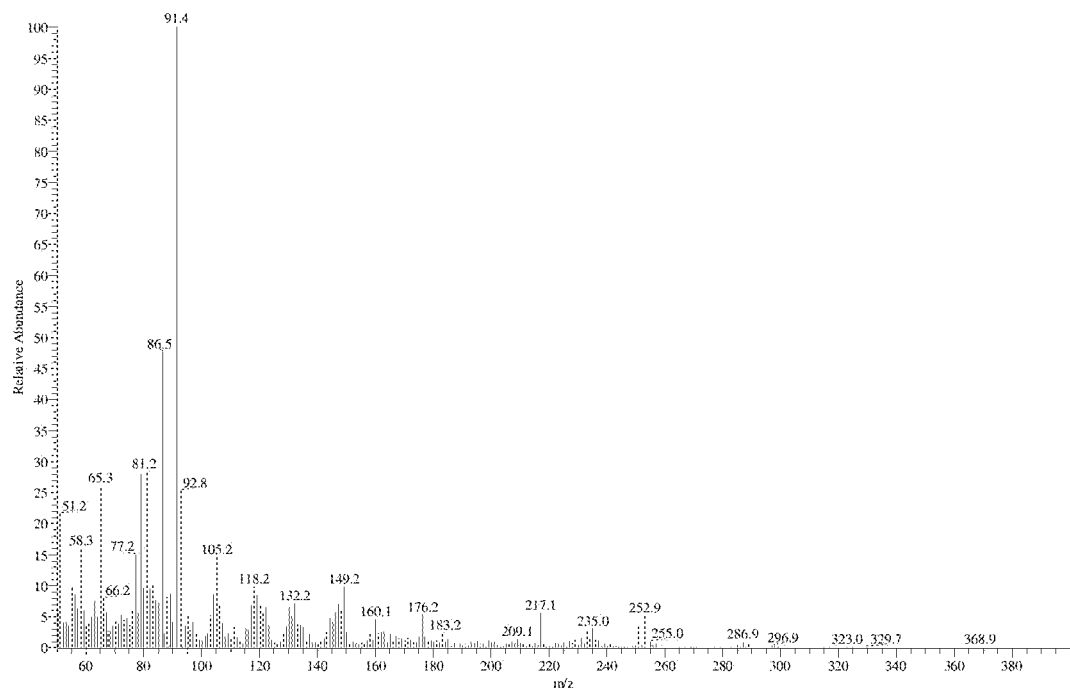
FIGS. 10A-10C are mass spectra of stable products of bromine-sensitized photolysis of $CO_2$, after storage at −20° C. for several weeks.
Figure 10B:
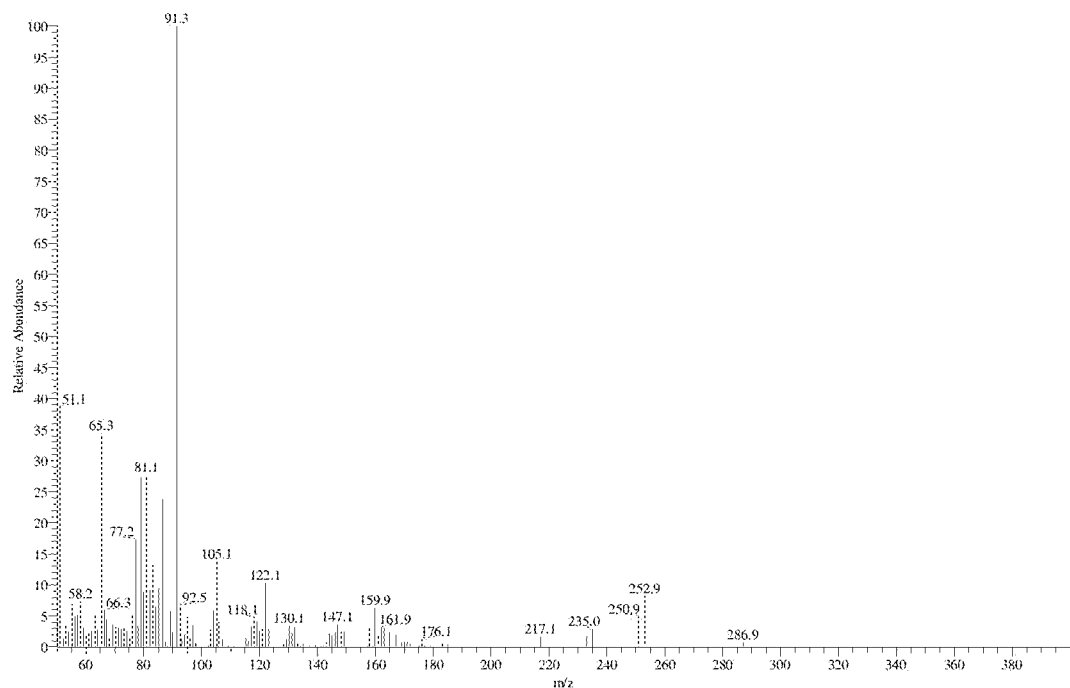
Figure 10C:
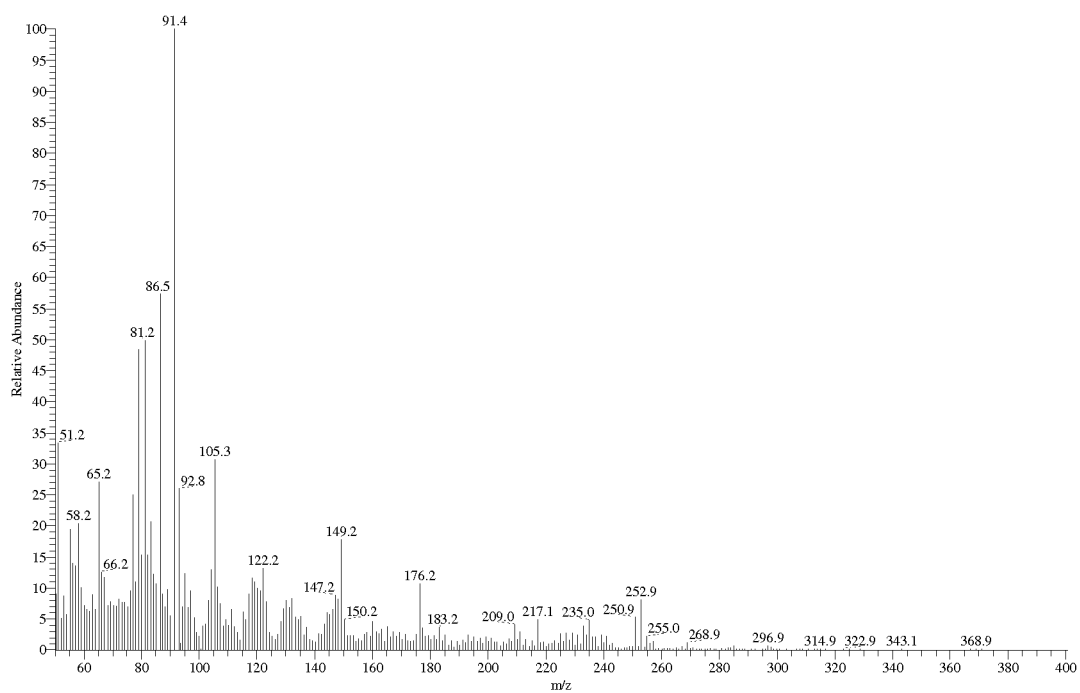

FIGS. 10A-10C are mass spectra of stable products of bromine-sensitized photolysis of $CO_2$, after storage at −20° C. for several weeks. Each mass spectrum represents an integration of the results obtained between 10.60 and 12.31 min, when the probe temperature was in the range 350°-400° C. Each of FIGS. 10A, 10B and 10C represents measurements on three independent samples produced on different days, using either quartz wool or glass wool as the polar adsorbent.

Figure 11A:
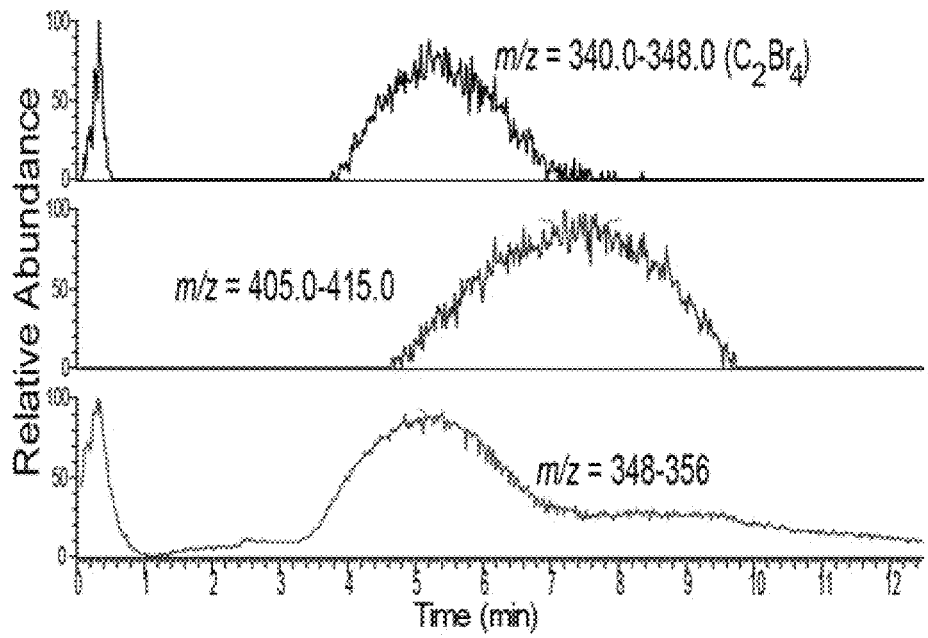
FIGS. 11A and 11B are mass spectra of stable products of bromine-sensitized photolysis of $CO_2$, after storage at −20° C. for several weeks.
Figure 11B:
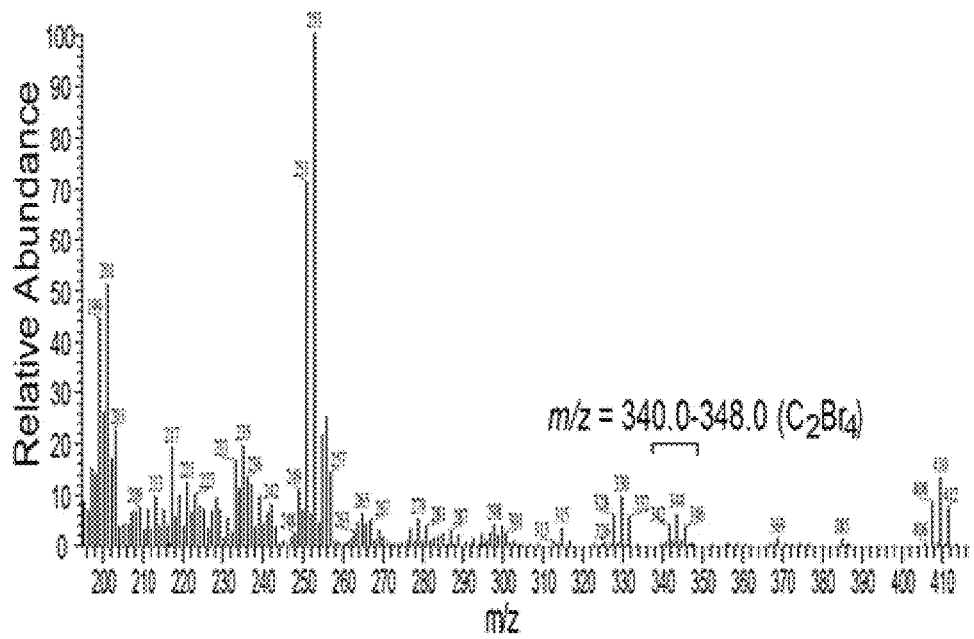

FIGS. 11A and 11B are mass spectra of stable products of bromine-sensitized photolysis of $CO_2$, after storage at −20° C. for several weeks; these were obtained using the same sample as FIG. 10A. FIG. 11B represents an integration of the results obtained between 4 and 10 min, when the probe temperature was increasing from 60°-350° C. The three panels in FIG. 11A show the time courses of the signals at 3 different m/z ratios, as indicated. Based on the observed set of isotope peaks and the temperature range at which the signals are observed, the peaks at m/z=340-348 are attributed to a $C_2Br_4$ being produced by the bromine-sensitized solar photolysis reaction of $CO_2$.

Although the foregoing invention has been described in some detail for purposes of illustration, it will be readily apparent to one skilled in the art that changes and modifications may be made without departing from the scope of the invention described herein.

What is claimed is:

1. A method for reducing carbon in $CO_2$, comprising, while contacting a mixture of $CO_2$ and $Br_2$ with a polar substrate presenting surfaces having points of contact between said surfaces, exposing a sufficient area of said mixture in the region of said points of contact to light of sufficient intensity and of suitable wavelengths to result in reduction of the carbon in said $CO_2$.

2. A method according to claim 1, wherein said polar substrate is a non-carbonaceous polar substrate.

3. A method according to claim 2, wherein said polar substrate is selected from the group consisting of silica, silica-based glasses, alumina and titania, and mixtures thereof.

4. A method according to claim 3, wherein said polar substrate is in particulate form.

5. A method according to claim 3, wherein said polar substrate is selected from sand, silica gel, powdered alumina, titania, quartz sand, glass spheres, and glass wool.

6. A method according to claim 1, wherein the light is a mixture of UV and visible light.

7. A method according to claim 6, wherein the mixture of UV and visible light includes light in the wavelength range of 300 to 500 nm.

8. A method according to claim 1, wherein said light is provided as sunlight.

9. A method according to claim 8, wherein said sunlight is focused onto said mixture in said region of said points of contact.

10. A method according to claim 9, wherein said sunlight is focused using a parabolic or paraboloid mirror.

11. A method according to claim 1 wherein the $CO_2$ is present in both liquid and gaseous phases.

12. A method according to claim 1, wherein the ratio of $Br_2$ to $CO_2$ is between 1:1 and 1:1000 by weight.

13. A method according to claim 1, wherein the polar substrate, $CO_2$ and $Br_2$ and are contained in a UV and visible-light transparent region of a reaction vessel.

14. A method according to claim 13 wherein the reaction vessel is made from quartz or borosilicate glass.

15. A method according to claim 13, wherein the pressure in the reaction vessel is between 1 and 71 bar.

16. A method according to claim 13, wherein the $CO_2$ is predominantly in the form of a gaseous phase.

17. A method according to claim 1, wherein the range of transparency of said UV and visible-light transparent region includes wavelengths of light from 300 to 500 nm.

18. A method according to claim 1, wherein the $CO_2$ is predominantly in the form of a liquid phase.

19. A process which comprises, while contacting a mixture of $CO_2$ and $Br_2$ with a polar substrate presenting surfaces having points of contact between said surfaces, exposing a sufficient area of said mixture in the region of said points of contact to light of sufficient intensity and of suitable wavelengths to result in reduction of the carbon in said $CO_2$, wherein a transient intermediate product of the process is a chemical compound of the formula $C_2O_4Br_4$.

20. The process of claim 19, wherein said chemical compound of formula $C_2O_4Br_4$ is a substituted 1,3-dioxetane.

* * * * *